United States Patent [19]

Kertz

[11] Patent Number: 5,171,683
[45] Date of Patent: * Dec. 15, 1992

[54] INTEGUMENT AND METHOD FOR MICROPROPAGATION AND TISSUE CULTURING

[75] Inventor: Malcolm G. Kertz, Sealy, Tex.

[73] Assignee: Agristar, Inc., Conroe, Tex.

[*] Notice: The portion of the term of this patent subsequent to Mar. 13, 2007 has been disclaimed.

[21] Appl. No.: 672,736

[22] Filed: Mar. 21, 1991

Related U.S. Application Data

[63] Continuation of Ser. No. 207,405, Jun. 14, 1988, abandoned, which is a continuation-in-part of Ser. No. 21,408, Mar. 4, 1987, Pat. No. 4,908,315.

[51] Int. Cl.⁵ .................... C12N 5/00; C12M 1/16; C12M 1/12; C12M 1/04; A01H 1/00; A01G 9/02
[52] U.S. Cl. .................... 435/240.4; 435/299; 435/311; 435/313; 47/58; 47/66; 47/84
[58] Field of Search .............. 435/240.4, 299, 311, 435/313; 47/58, 66, 84, 87

[56] References Cited

U.S. PATENT DOCUMENTS

| | | | |
|---|---|---|---|
| 2,934,204 | 4/1960 | Pardee | 206/46 |
| 2,994,424 | 8/1951 | Selby et al. | 206/46 |
| 3,022,605 | 2/1962 | Reynolds | 47/58 |
| 3,160,986 | 12/1964 | Watson et al. | 47/58 |
| 3,168,887 | 2/1965 | Bodell | 119/3 |
| 3,172,234 | 3/1965 | Eavis | 47/16 |
| 3,184,395 | 5/1965 | Brewer | 195/80 |
| 3,256,941 | 6/1966 | Rivman | 229/62 |
| 3,320,697 | 5/1967 | Larsen | 47/34.11 |
| 3,323,640 | 6/1967 | Kugler | 206/47 |
| 3,372,513 | 3/1968 | Shlesinger et al. | 47/58 |
| 3,384,993 | 5/1968 | Kane | 47/58 |
| 3,395,486 | 8/1968 | Campbell et al. | 47/34 |
| 3,524,279 | 9/1967 | Adams | 47/34.13 |
| 3,565,041 | 2/1971 | Brooks | 119/3 |
| 3,613,809 | 10/1971 | Coburn | 47/38 |
| 3,824,998 | 7/1974 | Snyder | 128/157 |
| 3,869,828 | 3/1975 | Matsumoto | 47/34.11 |
| 3,941,662 | 3/1976 | Munder et al. | 195/127 |
| 3,955,317 | 5/1976 | Gudin | 47/1.2 |
| 3,971,160 | 7/1976 | Vajtay | 47/34.11 |
| 4,006,561 | 2/1977 | Thoma et al. | 47/58 |
| 4,024,670 | 5/1977 | Stanley | 47/73 |
| 4,034,508 | 7/1977 | Dedolph | 47/84 |
| 4,063,383 | 12/1977 | Green | 47/1.1 |
| 4,075,785 | 2/1978 | Jones | 47/64 |
| 4,118,890 | 10/1978 | Shore | 47/28 |
| 4,170,301 | 10/1979 | Jones et al. | 206/423 |
| 4,189,868 | 2/1980 | Tymchuck et al. | 47/84 |
| 4,249,341 | 2/1981 | Huegli | 47/14 |
| 4,251,951 | 2/1981 | Heinstedt | 47/39 |
| 4,299,921 | 11/1981 | Youssef | 435/298 |
| 4,311,477 | 1/1982 | Kitamura et al. | 47/1.1 |
| 4,311,742 | 1/1982 | Otsuka | 428/35 |
| 4,400,910 | 8/1983 | Koudstaal et al. | 47/84 |
| 4,407,092 | 10/1983 | Ware | 47/64 |
| 4,424,645 | 1/1984 | Rannali | 47/66 |

(List continued on next page.)

FOREIGN PATENT DOCUMENTS

| | | |
|---|---|---|
| 0031985 | 7/1981 | European Pat. Off. . |
| 0042697 | 12/1981 | European Pat. Off. . |
| 2906959 | 8/1979 | Fed. Rep. of Germany . |
| 2324365 | 4/1977 | France . |
| PCT/GB87/-00218 | 4/1987 | PCT Int'l Appl. . |
| 8806402 | 9/1988 | PCT Int'l Appl. . |
| 1530705 | 11/1978 | United Kingdom . |

OTHER PUBLICATIONS

Technical Data Sheet CCO 9506-586 of the Chevron Chemical Company, 1986.
Technical Data Sheet CCO 5754-486 of the Chevron Chemical Company, 1986.
J. H. Dodds and L. W. Roberts, Experiments in Plant Tissue Culture (Cambridge University Press 1982) at Chapter 2, pp. 10-20.

(List continued on next page.)

*Primary Examiner*—David T. Fox
*Attorney, Agent, or Firm*—David A. Rose

[57] ABSTRACT

An integument and related process for the micropropagation of tissue and for the culturing of other organic matter is made of a translucent and semipermeable membrane.

18 Claims, 6 Drawing Sheets

U.S PATENT DOCUMENTS

| | | | |
|---|---|---|---|
| 4,460,632 | 7/1984 | Adur et al. | 428/35 |
| 4,463,522 | 8/1984 | Lindemann | 47/58 |
| 4,487,791 | 12/1984 | Komatsu et al. | 428/35 |
| 4,528,228 | 7/1985 | Clevenger | 428/74 |
| 4,562,663 | 1/1986 | Redenbaugh | 47/58 |
| 4,583,320 | 4/1986 | Redenbaugh | 47/57.6 |
| 4,615,883 | 10/1986 | Nelson et al. | 424/84 |
| 4,634,674 | 1/1987 | Shahin | 435/240 |
| 4,637,061 | 1/1987 | Riese | 383/38 |
| 4,637,163 | 1/1987 | Pellinen | 47/1.1 |
| 4,908,315 | 3/1990 | Kertz | 435/240.4 |
| 4,937,115 | 6/1990 | Leatherman | 428/36.4 |

OTHER PUBLICATIONS

Y. Yamada, "Photosynthetic Potential of Plant Cell Cultures" appears in Advances in Biochemical Engineering/Biotechnology (1985) pp. 89–98.

"Gardening with Plastics" by George Taloumis; Horticulture Magazine; Sep. 1953; pp. 369–380; vol. 31, No. 9.

"Film on the Farm" no author listed; Modern Plastics; Sep. 1956 p. 112, vol. 34, No. 1.

"Vertical Bag System used for mother foliage pot plants culture," by O. Marfa, T. Ramos, M. Jover & R. Save, Acta Horticult. vol. 178 1986 pp. 245–256.

"A New Exposure Model for In Vitro Testing of Effects of Gaseous Pollutants on Mammilian Cells by Means of Gas Diffusion Through Plastic Films" (G. Alink) Chemosphere 2:63–73. 1979.

"Comparative Growth Characteristics of Vero Cells on Gas-Permeable and Conventional Supports", Experimental Cell Research 84 (1974) pp. 271–281 (Jensen).

"A Device for Cultivation of Plant and Animal Cells,", Biotechnology Letters vol. 7, No. 7 (1985), pp. 467–470 (Jan Kybal et al).

Chevron Chemical Company, 1986, "Technical Data Sheet: Chevron Polyethylene Resins for Extrusion".

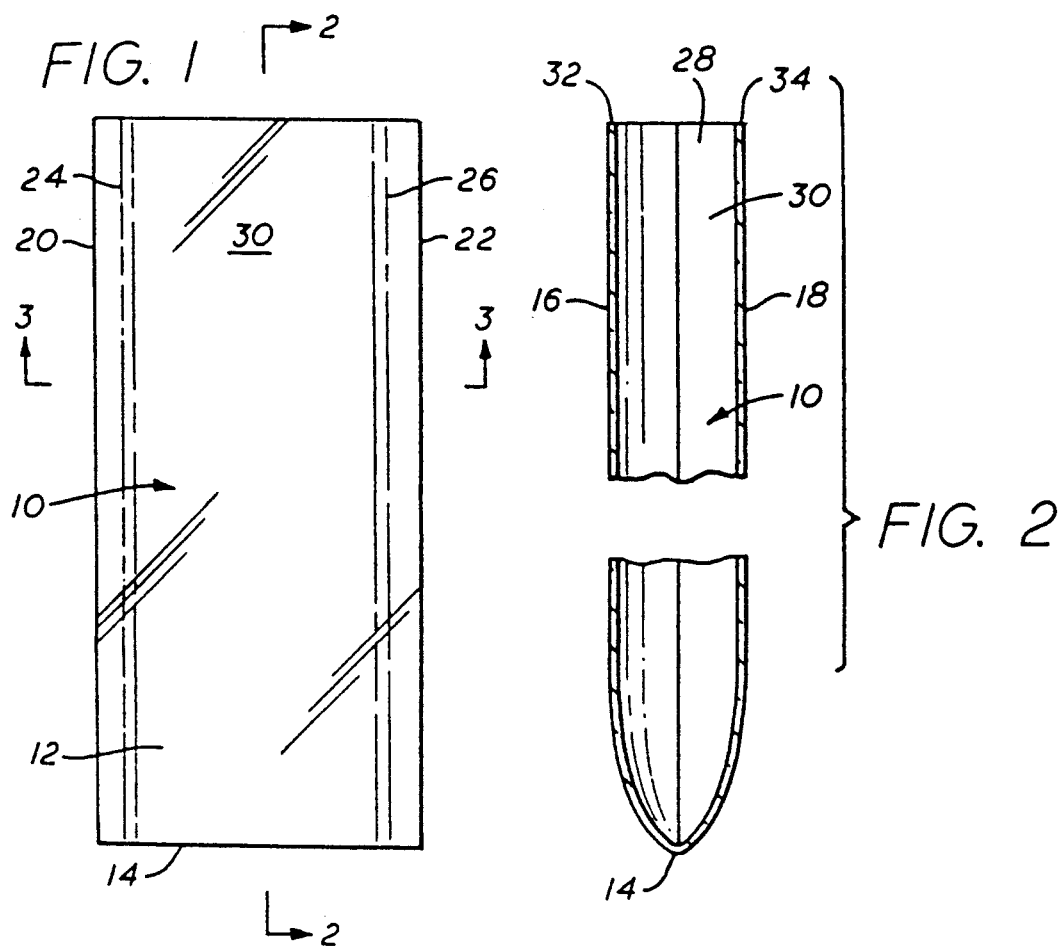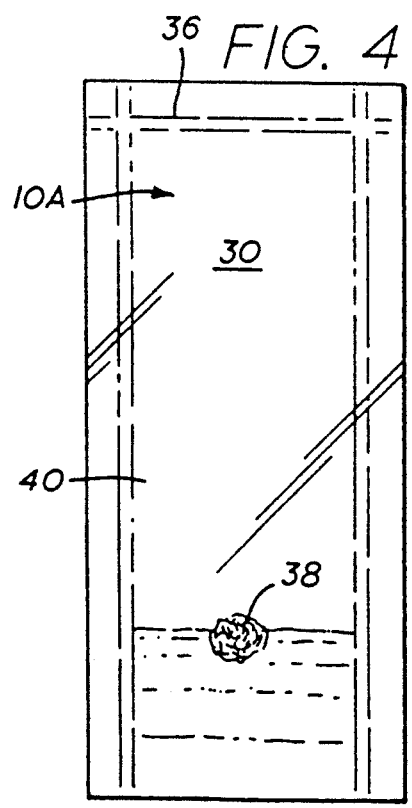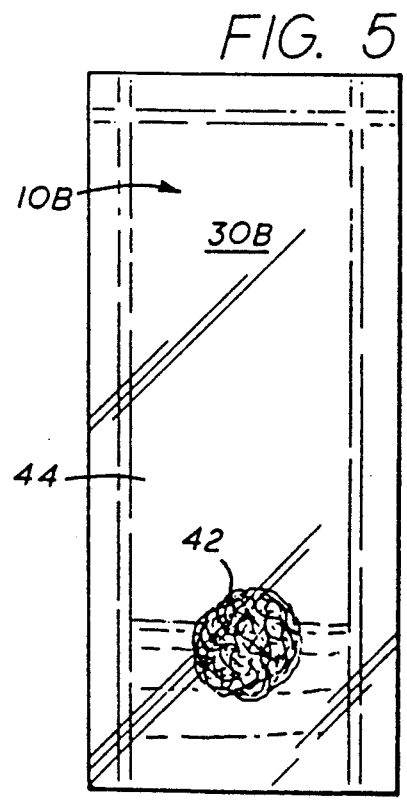

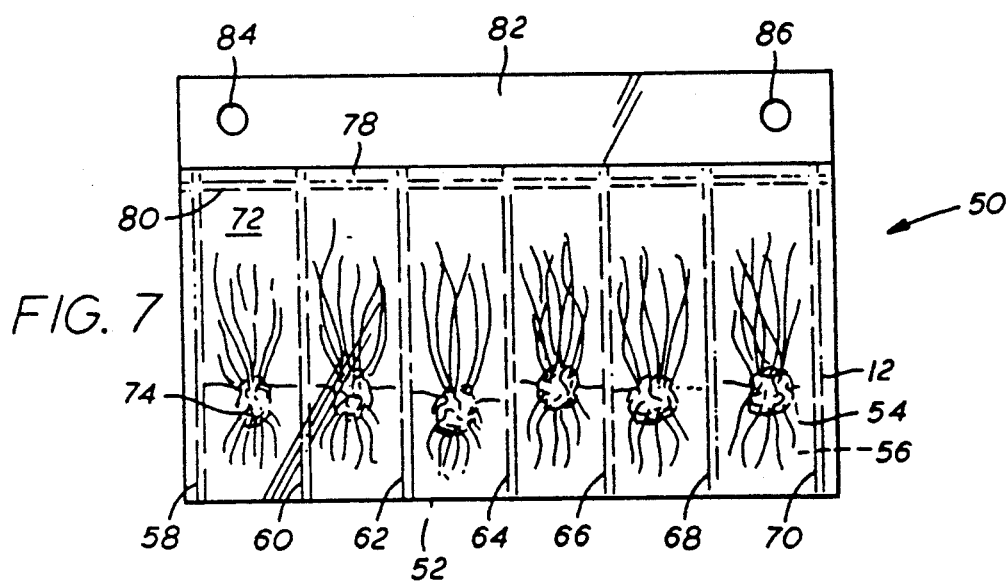
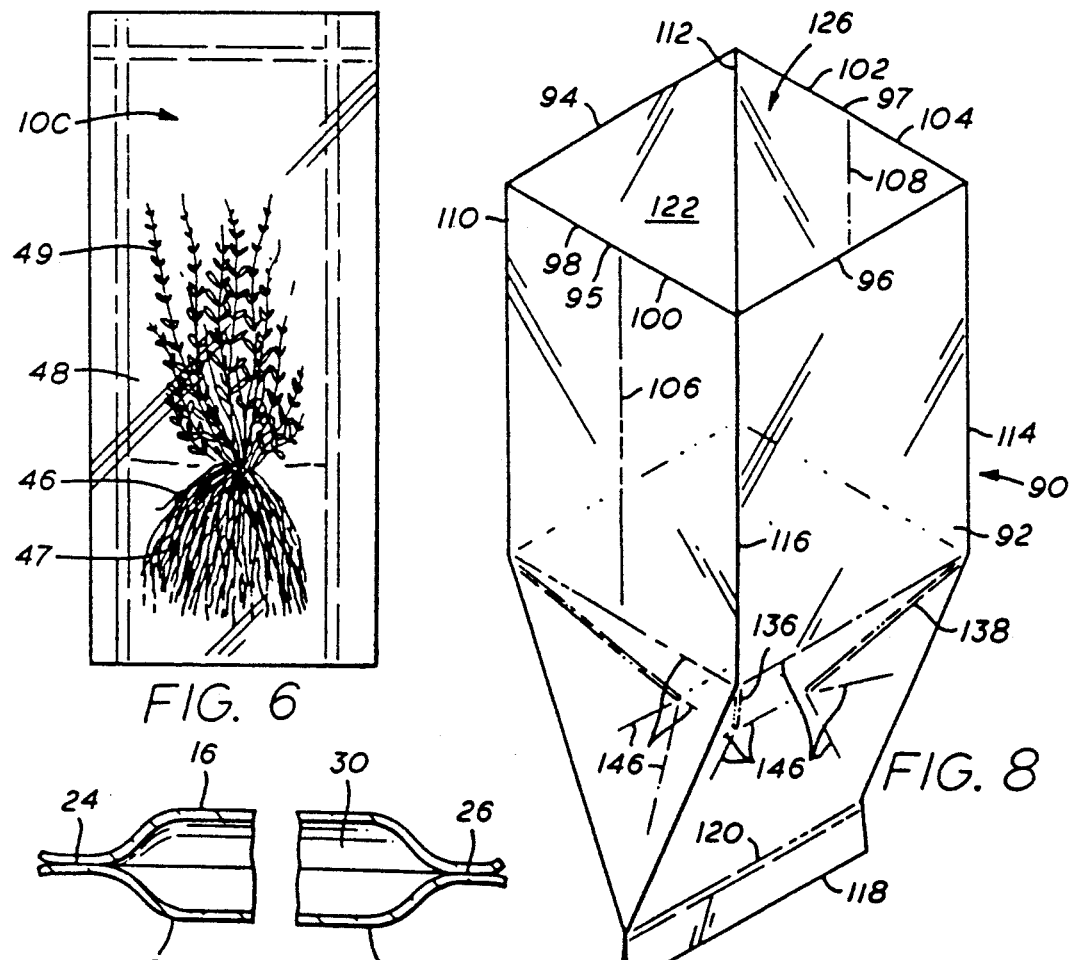
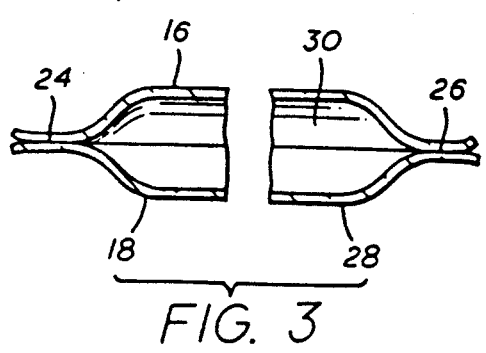

INTEGUMENT AND METHOD FOR MICROPROPAGATION AND TISSUE CULTURING

This is a continuation of copending application Ser. No. 07/207,405 filed on Jun. 14, 1988 now abandoned, which is a continuation-in-part of application Ser. No. 07/021,408 filed Mar. 4, 1987, now U.S. Pat. No. 4,908,315.

FIELD OF THE INVENTION

The present invention relates to a new and improved integument and method for micropropagation, tissue culturing and the culturing of other organic material. More particularly, the invention relates to a new and improved integument and method for enhancing the growth and reproduction of plant and animal cells and tissue, bacteria and other microorganisms, and for preventing contamination from occurring in the cultures.

BACKGROUND OF THE INVENTION

Micropropagation is the process of growing new generation plants from a single tissue sample that has been excised from a carefully selected parent plant or cultivar. This process permits the mass reproduction of plants having certain desirable traits since substantially all of the new generation plants produced are genetically identical to and have all the desirable traits of the parent.

Tissue culturing is the process of growing cells in vitro and is used to grow both plant and animal cells. Tissue culturing techniques are commonly used in the early stages of the plant micropropagation process where it is desirable to rapidly produce plant cells. Improvements in tissue culturing techniques also have applications beyond the micropropagation of plants. Essentially the same culturing process is used to culture animal and even human tissue, such tissue being used in the fields of animal agriculture and human and veterinary medicine. Culturing of organic material other than plant and animal cells and tissue, such as bacteria, viruses and algeas, is also performed in vitro for both research and commercial purposes. Improvements in the procedures and apparatus used to reproduce and maintain these organisms would be beneficial, for example, to researchers and industry who require a large or steady supply of such material.

There are problems associated with the prior art culturing apparatus and processes One of the primary problems is contamination. Any of a wide variety of microorganisms, including viruses, bacteria, fungus, molds, yeast and single cell algae, can ruin the cultures during any of the various stages. The smallest of these biological contaminants are the viruses, the largest are the single cell algae. A virus typically ranges in size from 0.1 to 0.45 micrometers although it is suspected that portions of the virus which are as small as 0.01 micrometers may separate from the virus and alone cause contamination. Bacteria typically range in size from 5 to 100 micrometers, while fungi and molds are usually larger than 100 micrometers. Yeast is larger than bacteria, with single cell algae, the largest of these biological contaminants, being larger than yeast.

The prior art sterilized glass or plastic culture containers such as test tubes, flasks or bottles, utilized in conventional culturing technology have serious drawbacks. For example, since plants require both carbon dioxide and oxygen to live and grow, these containers must provide a means for gas exchange. The walls of these traditional glass and plastic containers, however, do not permit the required gaseous interchange. Thus, rubber stoppers having cotton packing or some similar filter material, loosely fitting caps, or baffled plastic caps have been employed to allow an adequate exchange of gas between the tissue or plant and the ambient atmosphere and environment. However, such devices restrict the amount and rate of gas which can be exchanged. Further, such caps and stoppers do not totally protect the plant from contamination by microorganisms such as viruses, bacteria and fungi. Thus, it has been of paramount importance that the tissue culture room and laboratory be kept extremely clean and their atmospheres filtered. Further, precise temperature, humidity, and light conditions must be maintained in the culture room. Gas exchange is also required for culturing animal cells and for certain other microorganisms. Traditional flasks, petrie dishes and the like, while allowing for a certain degree of gas exchange, also allow contamination to occur.

The original cost of the traditional glass or plastic culture containers; the labor and equipment cost to maintain the sterility of the containers; and the added cost of the facilities, equipment, and related conditions required to maintain a sterile growing environment, all represent major cost factors associated with the use of such containers in conventional culturing processes.

The present invention overcomes many of the deficiencies of the prior art techniques of culturing by having the following advantages:

(1) enhanced protection from contamination;

(2) increased growth rates;

(3) no requirement for a sterile culture room;

(4) no requirement for expensive glass containers or the incurrence of replacement costs due to breakage;

(5) no labor cost associated with cleaning and sterilizing containers for reuse;

(6) an increase in the number of plantlets from a culture;

(7) a reduction by approximately one-half the amount of media required in each plant culture;

(8) the elimination of the requirement of strict humidity control in the culture room;

(9) an increase in the number of cultures which can be produced in the same size culture room;

(10) a reduction in the size of the media preparation area and in the size of the autoclave; and

(11) an increase in the number of new cultures which can be established by a laboratory technician.

Other objects and advantages of the invention will appear from the following description.

SUMMARY OF THE INVENTION

The present invention includes a new integument and related process for micropropagation, tissue culturing and for the culturing of other organic material. The integument is made of a semipermeable and translucent membrane which allows light transmission and gas exchange but seals out the biological contaminants in the ambient environment. The membrane forms a plurality of cellules which contain the organic samples and media. The cellules are sealed so as to completely enclose and seal off the cultures from the ambient environment. The most preferred membrane is a high density polyethylene material.

One of the principal advantages of the present invention is that biological contaminants in the ambient atmosphere cannot penetrate the membrane of the integument and thereby contaminate the culture. Yet, the semipermeable membrane ensures enhanced gas exchange, gas exchange being necessary for plant and animal cells and many microorganisms to live and reproduce. Because the integuments are contaminant impermeable, organic material contained therein need not be cultured in a sterile environment, and the costs and problems associated therewith are eliminated. Similarly, because the integument will not allow bacteria, viruses, and other microorganisms from the ambient environment to penetrate the membrane, the integument may also be used to culture a specific microorganism. The integument prevents the microorganisms grown or maintained therein from escaping the integument and possibly infecting laboratory personnel and, at the same time, prevents microorganisms in the ambient environment from contaminating the culture of the desired microorganisms contained in the integument.

The integument of the present invention is also liquid impermeable so that the media, typically a liquid or semisolid which sustains the tissue, organism, or plant's growth while in the integument, cannot escape and dry out. Thus, using the present invention, it is also unnecessary to maintain a precise humidity level in the culture room which would again require special and costly equipment.

A completely unexpected benefit of using the semipermeable integument is that tissue and plantlet growth rates are dramatically increased. This increase is believed to occur because oxygen and carbon dioxide, which are needed for plant respiration and photosynthesis and for sustaining certain bacteria, are available in greater quantities than when the process is carried out in prior art glass and plastic containers where the loose fitting lids, rubber stoppers, caps and filters, which are required to prevent the entrance of contaminants, impede gas exchange.

A preferred embodiment of this integument is formed from heat sealed high density polyethylene. This material has been found impermeable to contaminants and, because it is completely sealed once the organic sample is in place, the entire outer surface can be thoroughly decontaminated by emersion prior to opening the integument which exposes the culture to possible contamination. There are virtually no areas on the integument where contaminants can accumulate and avoid decontamination.

With the preferred embodiment of the invention, the costs of micropropagation and culturing are greatly reduced since the cost of the integument of the present invention is much less than the cost of prior art containers. The preferred integuments are, unlike glass test tubes, essentially unbreakable. Their low cost makes them completely disposable, eliminating the costs associated with washing and the often-less-than sterile product which results.

The apparatus of the invention has other applications other than the culturing of tissue and microorganisms. For example, improvements in growth rates were observed when the integuments were used in growing plants from seeds.

BRIEF DESCRIPTION OF THE DRAWINGS

For a detailed description of a preferred embodiment of the invention, reference will now be made to the accompanying drawings, wherein:

FIG. 1 depicts a frontal view of the integument of the present invention;

FIG. 2 depicts a partial elevation cross-sectional view of the integument of FIG. 1 taken along line 2—2 as shown in FIG. 1 with the material of the integument enlarged;

FIG. 3 depicts a partial top view of the integument of FIG. 1 with the material of the integument enlarged;

FIG. 4 depicts a meristematic tissue sample being cultured in the integument of FIG. 1;

FIG. 5 depicts the initial tissue culture from Stage 1 being multiplied during Stage 2 in a new integument of FIG. 1;

FIG. 6 depicts the growth of an individual plantlet during Stage 3 in a new integument of FIG. 1;

FIG. 7 depicts an integument pack with individual cellules of the type shown in FIG. 1;

FIG. 8 depicts a perspective view of an alternative embodiment of the integument of FIGS. 1 and 7;

DESCRIPTION OF THE PREFERRED EMBODIMENT

Figure 9:
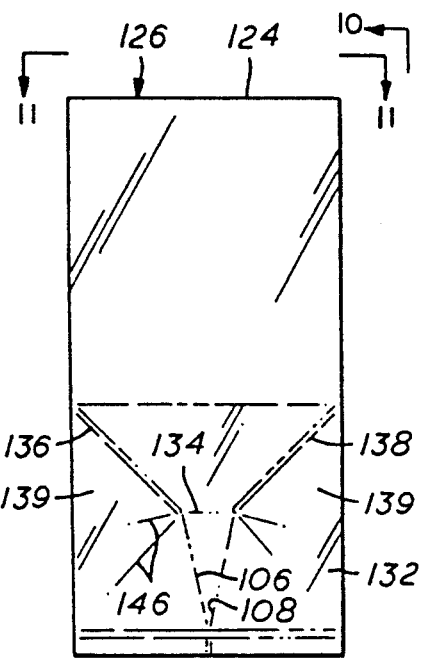
FIG. 9 depicts a front elevation view of the integument of FIG. 8 in the open position.

Referring initially to FIGS. 1, 2 and 3, there is shown the integument 10 of the present invention for containing and culturing organic material, such as, plant and animal tissue and cells and microorganisms including bacteria, viruses, fungus, molds and single cell algae. Integument 10 comprises membrane 12 which, in the preferred embodiment, encloses plant tissue from a parent plant or cultivar during the first three stages of micropropagation. However, it should be understood that the integument of the present invention may be used for culturing any type of organic material. When sealed, membrane 12 completely and entirely surrounds and encloses the culture from the ambient environment.

The integument 10 is made by folding membrane 12 over at 14 such that two sides 16, 18 are formed. Sides 16, 18 are heat sealed at 24, 26 along the entire length thereof and adjacent to longitudinal edges 20, 22 of membrane 12 so as to form an envelope. The envelope shaped integument 10 includes a cellule 30 forming an expandable chamber for containing the plant tissue and growth medium. The cellule 30 has an approximate average volume of 50 ml for most varieties of plants. As can be appreciated, the size and volume of the chamber of cellule 30 can be varied to host the particular tissue or plantlet contained therein. Thus, cellule 30 may be of various sizes. The cellule 30 has at least initially, an open end 28 formed by the terminal edges 32, 34 of membrane 12. End 28 serves as a port of entry of cellule 30 for receiving the plant tissue and media. As can also be appreciated, rather than being made of a single folded membrane 12, integument 10 may be made of two individual and separate pieces of material such as a base material and a frontal material. In this embodiment, the bottom of cellule 30 is formed by heat sealing the frontal material to the base material near the lower terminal edges thereof as distinguished from the fold at 14 where a single piece of material is used as described with respect to FIGS. 1-3. Composite integuments may be formed to take advantage of the strength of one material and the permeability to oxygen and carbon dioxide of the other, as an example.

The membrane 12 is a polyethylene material which is pliable and collapsible such that it can be stored and shipped in rolls. Further, the polyethylene is so inexpensive as to be disposable upon completion of any particular stage of the microproagation process. Preferably, the membrane 12 is made of high density polyethylene. Such polyethylene typically has a density of from 0.94 to 0.96 gm/cc density polyethylene. The material for membrane 12 should withstand sterilization in an autoclave which may reach temperatures of 250° F. at 15 p.s.i., for example.

Referring now to FIGS. 4 to 6, the integument 10 is shown in each of the first three stages of micropropagation. As is shown, after the plant tissue and media have been received by cellule 30, the port of entry at open end 28 is heat sealed at 36 along the entire length thereof and adjacent to the terminal edges 32, 34 of membrane 12 to close and seal cellule 30 containing the plant tissue and media therein. At this time the plant tissue is completely and entirely encapsulated from the ambient environment and sealed from biological contaminants in the ambient environment. FIGS. 4 to 6 schematically illustrate the integuments 10A, B and C investing the plant tissue and media in each of the first three stages of micropropagation. FIG. 4 depicts the meristematic tissue 38 from a parent plant or cultivar invested within integument 10A together with suitable media 40 such as Murashige Minimal Organic Medium manufactured by Carolina Biological Supply Company. FIG. 5 illustrates the use of another integument 10B during the second stage of tissue culturing. The initial tissue culture 42 from Stage 1, or a portion of such tissue, is transferred to cellule 30B containing a suitable Stage 2 medium 44 such as Murashige Shoot Multiplication Mediums A, B and C manufactured by Carolina Biological Supply Company. FIG. 6 shows an individual plantlet 46 grown in Stage 2 enclosed by another integument 10C and placed in a medium 48 such as Murashige Pretransplant Medium manufactured by Carolina Biological Supply Company to stimulate cell differentiation and the growth of individual plantlets such as 46, each plantlet 46 developing roots 47 and foliage 49.

Although the integument 10 has been shown and described as providing a single cellule 30 for enveloping an individual culture, it is preferred that the integument form a plurality of cellules. Referring now to FIG. 7, there is shown an integument pack 50. Integument pack 50 is made of membrane 12 and is formed similarly to integument 10 of FIG. 1. For most culture investments, the integument pack 50 has dimensions of approximately 12 inches wide and 6 inches high. Integument pack 50 is formed by folding membrane 12 over at 52 so as to form sides 54, 56. As distinguished from integument 10, sides 54, 56 are heat sealed along the entire longitudinal length thereof at 58, 60, 62, 64, 66, 68 and 70 to form six individual cellules 72. Individual tissue samples 74 and media 76 are shown invested in each of the cellules 72. The plant tissue and media may be for any of the first three stages of micropropagation as represented in FIGS. 4 to 6. The ports of entry at the upper end 78 have been heat sealed at 80 along the entire length of integument pack 50 to close cellules 72 after the tissue 74 and media 76 are inserted into the cellules 72. An upper flap or band 82 may be formed at the upper ends 78 of membrane 12 for the purpose of suspending integument pack 50 in the vertical position. Suitable connection means such as apertures 84, 86 may be provided through band 80 for attachment means such as drapery hooks or S-hooks to suspend integument pack 50 vertically. Suspending the growing tissue and plants vertically at different elevations markedly reduces the amount of space required in the growing areas. The suspension of cultures above others is allowed because of the translucency of integument packs 50. Further, the vertical suspension of integument packs 50 at different elevations will also enhance air movement within the growing area. Many conventional growing area layouts concentrate the tissue cultures or plants at a given elevation within the growing area, such as on countertops or working surfaces, such that there is a limited movement of air between the plants. Thus, by increasing light transmission and the availability of air for gas exchange by suspending integument packs 50, growth of the tissue and plants is enhanced and the growing area requirements are reduced.

The cellule, and thus the integument, is sized in accordance with the culture to be grown. Referring now to FIGS. 8 to 13, there is shown another embodiment of the integument shown in FIGS. 1 and 7 that is adapted and sized for the micropropagation of lettuce, spinach or other leafy vegetables. The integument 90 for enclosing the tissue for a leafy vegetable is made of a membrane 92, membrane 92 being like that of membrane 12 for integument 10 or integument pack 50 as shown in FIGS. 1 and 7 respectively.

Figure 12:
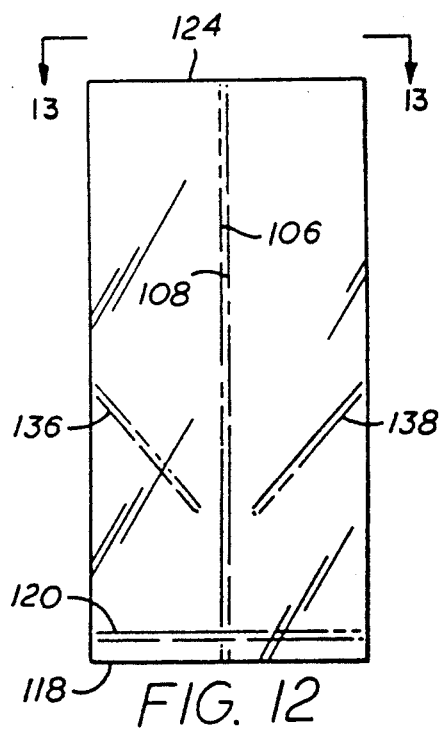
FIG. 12 depicts a front elevation view of the integument of FIG. 8 in the folded position.
Figure 13:
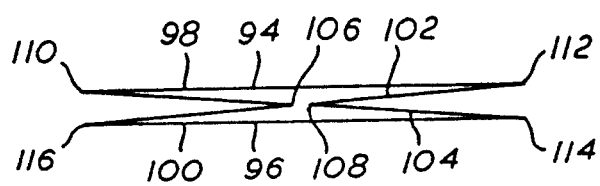
FIG. 13 depicts a top view of the integument shown in FIG. 12.

Integument 90 is made by membrane 92 being extruded in tubular form having a circumference of approximately 24 inches. The tubular membrane 92 is folded into quarter panels 94, 95, 96, 97 and one eighth panels 98, 100 and 102, 104, best shown in FIGS. 8, 11 and 13. One eighth panels 98, 100 and 102, 104 are formed by folding quarter panels 95 and 97 at 106 and 108, respectively. Quarter panels 94, 95, 96 and 97 were formed by folding tubular membrane 92 into quarter lengths, at folds 110, 112, 114, 116. Folds 106, 108 are directed inwardly as shown in FIG. 13 and one end 118 of tubular membrane 92 is heat sealed at 120 in the folded position as shown in FIG. 12 to produce a cellule 122 to house the leafy vegetable tissue and media. The cellule 122 has a volume of approximately 1000 ml which can be varied according to the particular leafy vegetable plant tissue grown therein. The other end 124 of tubular membrane 92 is initially left open as a port of entry 126 to receive the leafy vegetable tissue and media.

Figure 10:
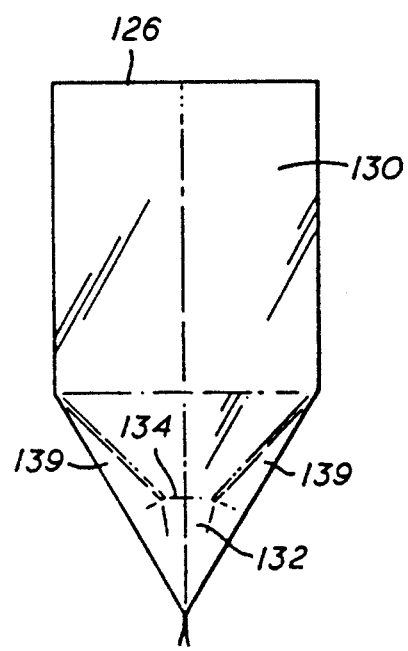
FIG. 10 depicts a side elevation view of the integument of FIG. 9 in the open position.
Figure 11:
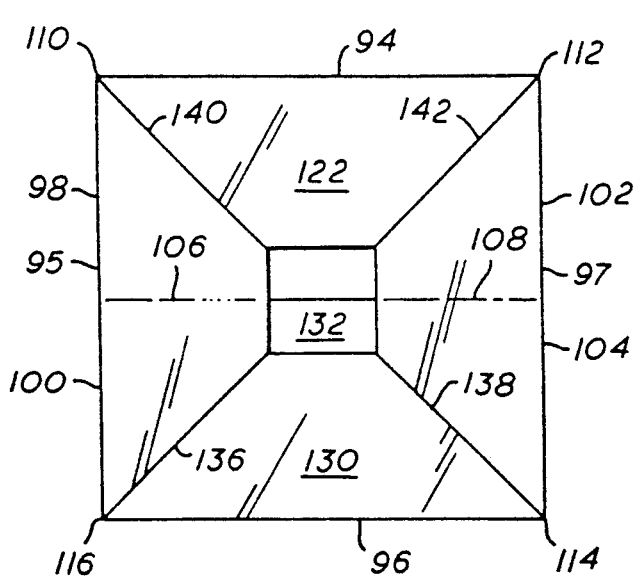
FIG. 11 depicts a top view of the integument of FIG. 9.

Cellule 122 preferably includes a foliage chamber 130 and a root chamber 132 with an open neck 134 therebetween, best shown in FIG. 10. Chambers 130, 132 and neck 134 are formed by heat sealing portions of one eighth panels 100 and 104 to quarter panel 96 at 136 and 138 and by heat sealing portions of one eighth panels 98 and 102 to quarter panel 94 at 140 and 142. Additionally, upon expanding integument 90, heat seals 136, 138 and 140, 142 create creases at 106, 108 and 146 shown in FIGS. 8 and 9 to form root chamber 132.

The foliage chamber 130 and root chamber 132 of cellule 122 permit a separation of the foliage from the root system during growth and more particularly to separate the foliage from the media. A plantlet is positioned within cellule 122 such that the foliage grows within foliage chamber 130 and the root system extends from the foliage chamber 130 down through neck 134 and into the root chamber 132 where the media is disposed. Given a cellule 122 with a volume of approximately 1000 ml, the root chamber 132 is sized to contain approximately 50 ml of media. By maintaining the integument 92 in the vertical position, all media will flow downward into root chamber 132. This downward flow is facilitated by the angular heat sealing at 136 and 138. Thus, the media is thereby kept separate from the foliage. This permits the foliage to be kept clean of media and to permit the leafy vegetable to grow in a preferred and desirable symmetric shape. Without the division of cellule 122 into a foliage and a root chamber, the leafy vegetable would grow in a haphazard form losing its symmetry. Further, with the reduced neck portion 134 separating cellule 122 into a root chamber 132 and foliage chamber 130, the media is retained in the root chamber 132 and its flow into the foliage chamber 130 is prevented or retarded when the integument 90 is tipped or inverted since the media will tend to flow into the upper angular portions 139 of root chamber 132 instead of flowing through neck position 132. Additionally, the reduced neck portion 134 tends to secure a mature plant in position within cellule 122 since the plant's roots will grow into a mass having a size larger than the cross sectional area of neck portion 134. This growth of root mass also acts to impede the flow of media into the foliage chamber 130.

The material for membrane 12 of integuments 10, 50 and for membrane 92 of integument 90 is critical to providing the desired environment for the tissue and plantlet during the first three stages of micropropagation and in particular enhancing growth by permitting optimum gas exchange and light transmission. Gas exchange, for example, is needed for the necessary biochemical actions required for culture growth. Understanding the role of the gases and gas exchange requires an explanation of the utilization of each gas individually.

Two functions of green plant growth are photosynthesis and respiration. Photosynthesis is the biochemical process where green plants convert carbon dioxide and water into complex carbohydrates in the presence of light of a given wave length and intensity for a given period of time. The process is affected by a number of environmental factors including quality of light, availability of water, availability of carbon dioxide, temperature, leaf age and chlorophyll content of the tissue. Photosynthesis is also referred to as a carbon dioxide fixation. The exact chemistry of the process is complex but in essence, chlorophyll in the presence of carbon dioxide, water and light converts the carbon dioxide and water into complex carbohydrates that are in turn converted into sugars and utilized by the plant as a food source.

One of the by-products of this process is the production of free oxygen. Fixation of carbon dioxide by plants accounts for a large portion of their carbon content and subsequent weight increase during growth. The exact uptake of carbon dioxide by plants varies from species to species. However, a range between eight and eighty milligrams of carbon dioxide per hour for 100 cubic centimeters of tissue surface can be used as an approximation of the carbon dioxide intake for most plants exposed to good environmental conditions. This intake can be directly related to the dry weight of plant tissue. At an uptake rate of 25 milligrams of carbon dioxide per hour for 100 cubic centimeters of tissue surface, an increase of 5% of the original weight of the tissue can be realized in a one hour period. From this overview of photosynthesis and carbon dioxide fixation, it is clear that among the critical factors affecting plant growth is the availability of carbon dioxide.

The other function relating to the gases of interest is respiration. This process is essentially an oxidation reduction reaction where oxygen serves as the oxidizer to the carbohydrates and sugars formed during the process of photosynthesis. Again, the exact chemistry involved is very complicated. However, the end result is a release of chemical energy necessary for continued growth of the plant. As in photosynthesis, or carbon dioxide fixation, a number of environmental factors affect the uptake of oxygen for the respiratory process. These include temperature, light, tissue starvation, availability of oxygen and tissue age. While respiration is believed to take place at all times in plant tissue, there is a noted increase in this activity in the absence of light. This is believed to be a result of the decreased creb cycle activity in the absence of light.

Oxygen uptake for use in respiration varies from species to species and while no generally accepted range has been established for plants in ideal environmental conditions, uptake of up to 350 microliters to 1,480 microliters per gram of fresh tissue has been recorded. There has been no direct correlation of fresh weight to oxygen uptake. There is also a difference in oxygen uptake from tissue to tissue within a given plant. Woody tissue and starch storage organs have the lowest uptake, while root tips and other regions containing meristematic cells have the highest uptake rate. This can be directly related to the activity of growth in a given area of the plant where the most active areas require the greatest energy production and consume the greatest amount of oxygen. From this, it is clearly defined that the presence of available carbon dioxide and oxygen is essential to the continued growth of green plant tissue.

In prior art micropropagation procedures, the exchange of oxygen and carbon dioxide between the plant tissue disposed within a glass or plastic container for protection from contamination has been severely limited in that the gas exchange must take place through the cotton packing disposed in the bore of the rubber stopper, between the loose fit of the top and the container and a plastic lid or top, or through the slits in the baffled plastic top. This curtailment of gas exchange has limited the growth of the plant tissue. The material of membranes 12, 92 provides a marked enhancement of permitted gas exchange as compared to the prior art glass or plastic containers.

The membranes 12, 92 are made of a translucent and semipermeable material. The preferred material for membrane 12, 92 is a high density polyethylene, material no. HiD-9650, manufactured by the Chevron Chemical Company of Orange, Tex. Preferably, the material for membrane 12, 92 should be from 1.0 to 2.0 mils thick, and it is preferred that the material of membrane 12, 92 have a thickness of 1.25 mils. If the membrane material is much thinner than 1.0 mil, handling the integument packs 50, and especially opening cellules 72, is made more difficult, as the opposing surfaces of the material of membranes 12, 92 tend to adhere to each other when formed in such thin films.

Other materials which have the desired light translucency, gas permeability and contaminant impermeability are also available for membranes 12, 92. For example, certain translucent low density polyethylene is suitable and even allows greater gas permeability than the preferred high density polyethylene; however, such low density polyethylene cannot withstand the high temperatures of the autoclave (250° at 15 p.s.i. for example) and the material melts or is otherwise deformed in the process. Accordingly, if such materials are used for membranes 12, 92, they and must be sterilized through other means.

Other polymeric materials may be used which have greater permeability than the preferred high density polyethylene; however, if the permeability is too great, the media drys out as the water in the media solution vaporizes and passes through membrane 12, 92 and out of the integument. Thus, the moisture vapor transmission rate (MVTR) is an important factor in the selection of materials for membranes 12, 92. It is preferred that membranes 12, 92 have a MVTR of from 0.2 to 0.684 gm/100 sq. in./24 hrs @ 1 atm. The preferred material, Chevron HiD-9650, in the preferred thickness of 1.25 mils, has a MVTR of 0.3 gm/100 sq. in./24 hours @ 1 atm. Membranes 12, 92 of other materials, thicknesses, and permeabilities can be used depending upon the length of time the plant material is to be grown in that integument. For example, the longer the growing period required for the particular plant material, the lower the MVTR of the material should be so as to prevent the media from drying out to a degree that it will not be conducive to growth.

The high density polyethylene at a thickness of 1.25 mils forms a molecular structure during the extrusion process which is especially useful as a membrane for integuments. The high density polyethylene is made from linear crystalline polymers of suitable molecular weight with high tensile strength and extension modulus, a high degree of symmetry, strong intermolecular forces and a controlled degree of cross-linking between layers. The cross-links between adjacent layers of polymers are introduced to prevent the polymeric chains from slipping under applied stress. The lightly cross-linked adjacent uniform layers of polymers of the high density polyethylene for membranes 12, 92 form interstices therebetween which allow the preferred diffusion and osmosis therethrough for the desirable gas exchange and light transmission between the ambient environment and the plant tissue. These interstices are smaller than 0.01 micrometers so as to preclude the passage therethrough of even the smallest microorganisms, such as viruses. It also provides rigidity to facilitate the transfer and handling of the cultures. Upon sealing off the cellule, the culture is completely enveloped and enclosed from the ambient atmosphere and environment, as distinguished from prior art containers, so as to prevent any introduction of contaminants.

The necessary gas exchange between the culture and the atmosphere of the ambient environment due to the production of the by-product oxygen by the plant during photosynthesis and the oxygen uptake of the plant during respiration takes place by osmosis. The gases diffuse or propagate through the semipermeable membrane 12, 92, which separates the miscible gases in the ambient atmosphere and within the cellule, in moving to equalize their concentrations. The osmotic pressure or unbalanced pressure between the ambient atmosphere and cellule gives rise to the diffusion and osmosis causing an interaction or interchange of gases by mutual gas penetration through the separating semipermeable membrane 12, 92. Thus, the inventive membrane of the integument permits the tissue to breathe by osmosis and air to diffuse through the semipermeable membrane and yet prevent the passage of biological contaminants.

The gas permeability of the material of membrane 12, 92 is thus also important. For practicing the invention described herein, it is preferred that the membrane material have a permeability to $CO_2$ of from 200 to 1190 cc/100 sq. in./24 hours at 1 atm. and a permeability to $O_2$ of from 100 to 424 cc/100 sq. in./24 hours at 1 atm. Chevron HiD-9650, the preferred material for membrane 12, 92, in the preferred 1.25 mil thickness has a permeability to $CO_2$ of approximately 450 cc/100 sq. in./24 hours at 1 atm. and a permeability to $O_2$ of approximately 190 cc/100 sq. in./24 hrs. at 1 atm.

The material of membranes 12, 92 is translucent and allows the passage and diffusion therethrough of light rays having at least the wavelengths of 400 to 750 nanometers. Individual wavelengths of light in the range of 400 to 750 nanometers are required by individual photosynthetic agents, such as the chlorophylls, in green tissue plants to provide the reactions necessary for life and growth. The reduced thickness of the material for membranes 12, 92 and the uniformity of molecular structure formed in part by the extrusion process for the material for membranes 12, 92 permits greater light transmission to the tissue sample enclosed by the integuments than has previously been allowed by the glass and plastic of prior art containers. The approximate 1.25 mil thickness of the material for membrane 12, 92 as compared to the much thicker prior art glass or plastic containers, substantially enhances the amount of light and the various individual wavelengths of light which are received by the tissue culture. It is important that each wavelength of light necessary for each photosynthetic agent to react pass through the integument. The uniformity and light cross-linking of the molecular structure of the material for membranes 12, 92 provides a pathway of lesser resistance for light. The molecular structure of glass and plastic of the prior art containers is more complicated and thus creates a more complex pathway through the glass or plastic through which the light must pass to ultimately reach the plant tissue. Thus the thicker and more complex molecular structure of the prior art glass and plastic containers inhibits light passage and may filter out certain wavelengths of light necessary for the photosynthetic agents of green tissue plants.

As stated, the preferred material for membranes 12, 92 is a high density polyethylene manufactured by the Chevron Chemical Company of Orange, Tex., Material No. HiD-9650. Published specifications for this polyethylene discloses it has a Melt Index of 0.3 (gms/10 min), Density of 0.950 (gms/cc); Dart Impact of 90 (gms/mil at 26"); Tensile strength at break of 7400 (psi); Elongation of 460%; Elmendorf Tear MD/TD of 16/400 (gms/mil); and a Moisture Vapor Transmission Rate (MVTR) of 0.35 (gms/100 sq. in./24 hr./mil).

Figure 14:
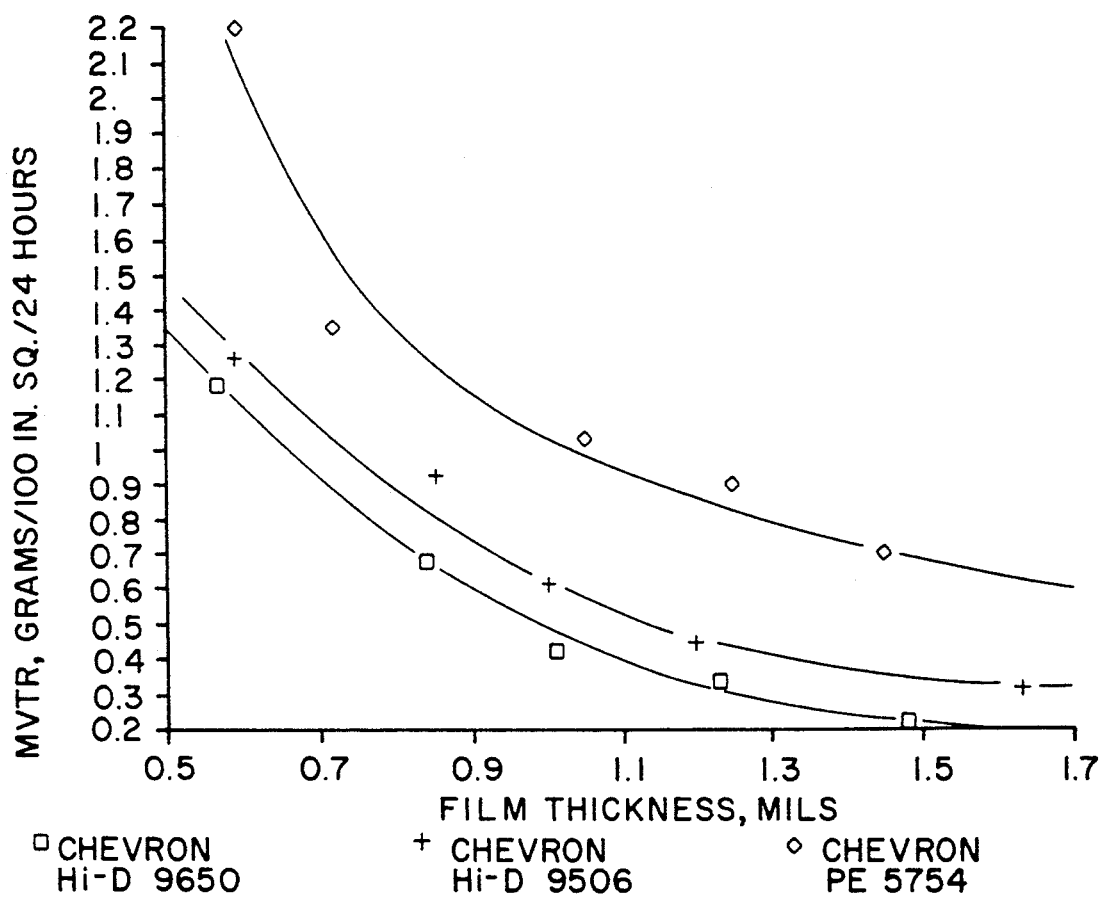
FIG. 14 is a graph showing the moisture vapor transmission rate of three different polyethylenes versus film thickness.
Figure 15:
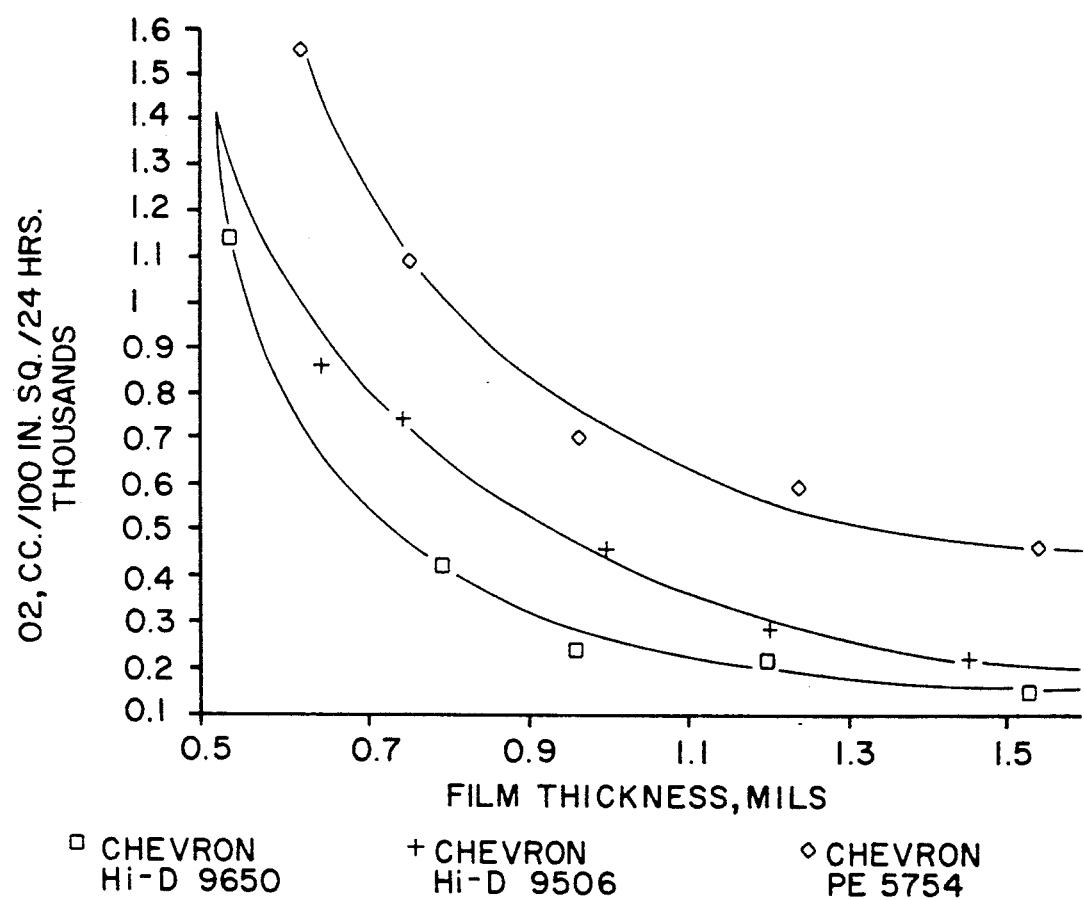
FIG. 15 is a graph showing the oxygen transmission rate of the three different polyethylenes in FIG. 14 versus film thickness.
Figure 16:
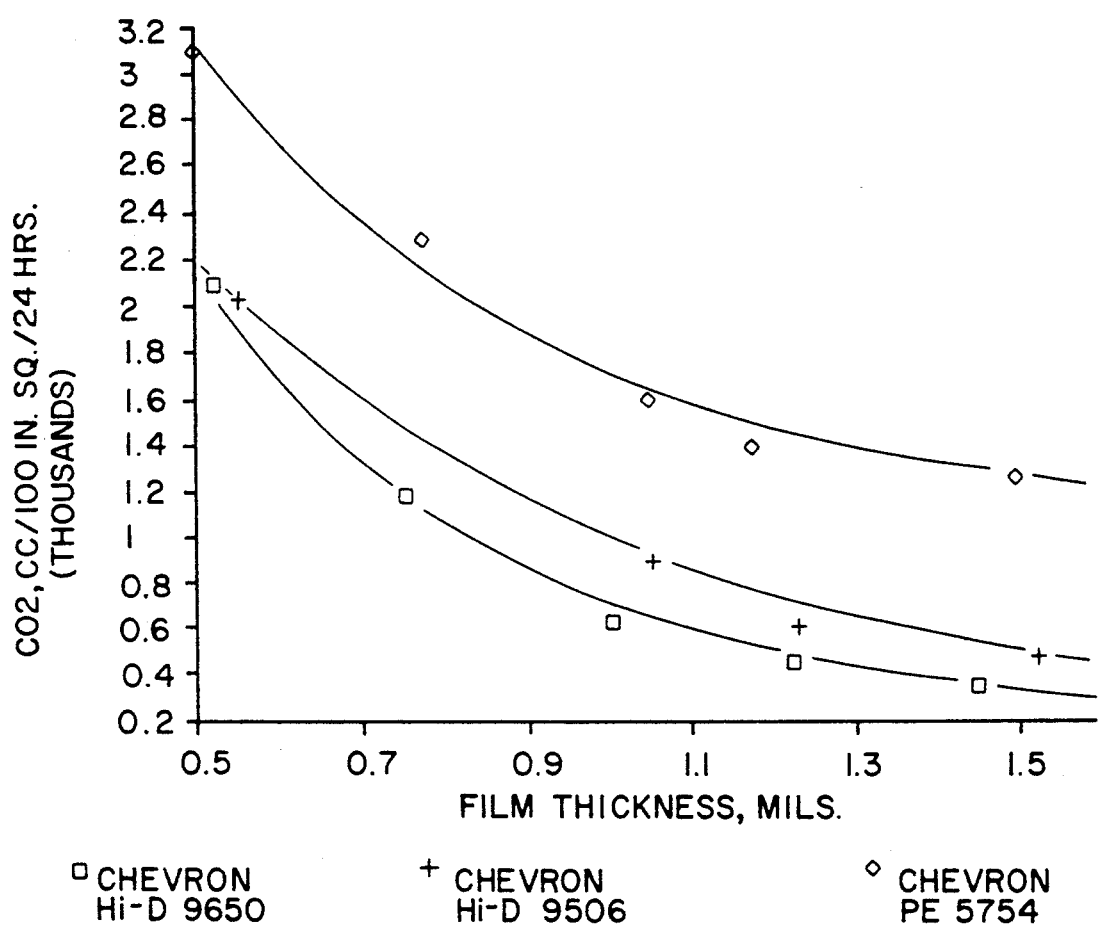
FIG. 16 is a graph of the carbon dioxide transmission rate of the three polyethylenes in FIGS. 14 and 15 versus film thickness.

Tests conducted at Applicant's direction demonstrate the transmission rates of water vapor, oxygen and carbon dioxide for various thicknesses of the preferred high density polyethylene (Chevron HiD-9650); another high density polyethylene (Chevron-9506); and a low density polyethylene (Chevron-PE5754). The results of these tests are included in FIGS. 14, 15, and 16. The results are also shown in tabular form in Table IV. As can be seen, the thinner the membrane, the greater its transmission rates for these gases. In addition, it can be seen that for the three membrane materials tested, the low density material (Chevron PE-5754) has the highest transmission rate for each of these gases. Although gas exchange is important to the growth of plants within integument 10, Applicant's preferred membrane made from Chevron's HiD-9650, has a lower transmission rate than the other materials tested as shown in FIGS. 14–16. As noted above, if the gas transmission rates are too great, the media in the integument 10 will dry out too quickly and the plant material will desiclate and die, possibly before it can complete a stage of development in the micropropagation process.

Table III illustrates plant growth rates where various thicknesses and types of materials were used as membranes 12, 92. As shown in Table III, growth rates were recorded when membranes of high density polyethylene (Chevron HiD-9650, Chevron-9506, Dupont-550) and low density polyethylene (Chevron-PE-5754) were used in an integument pack 50. To conduct this test, fifty integument packs 50 were obtained in each mil thickness shown in Table III for each of the four membrane materials (excluding 1.0 mil and 1.75 mil thicknesses of Chevron-PE-5754 which were not available). Under a laminar flow hood, equal amounts of media were placed in the cellules of each sterilized integument pack 50. Each cellule was then invested with a sample of plant tissue and the integument pack 50 was then sealed to prevent the introduction of contaminants. Integument packs 50 were then placed in the culture area of the laboratory. At thirty day intervals, each integument pack 50 was weighed, and an average weight of an integument was calculated for each of the fifty samples of the same membrane material and the same mil thickness. This data was recorded and is reproduced in Table III. After one hundred eighty days of the experiment, the thirty day average weight was subtracted from the last recorded weight and the difference was recorded in Table III below the one hundred eighty day weight. As can be seen, the preferred membrane 12, 92 of Chevron high density polyethylene HiD-9650 enabled plant material to grow at greater rates and for longer periods of time than the other materials tested.

The new and improved integument of the present invention permits the utilization of a new and improved process for micropropagation. This process includes four stages as hereinafter described.

TABLE 3

| | | PLANT GROWTH RATES | | | |
|---|---|---|---|---|---|
| MILS | DAYS | CHEVRON 9650 | CHEVRON 9506 | DUPONT 550 | CHEVRON 5754 |
| 1.0 | 30 | 25.28 gms | 23.06 gms | 24.37 gms | ND |
| | 60 | 27.58 | 23.61 | 24.98 | ND |
| | 90 | 33.42 | 24.27 | 23.21 | ND |
| | 120 | 36.01 | — | 23.61 | ND |
| | 150 | 39.89 | — | — | ND |
| | 180 | 41.98 | — | — | ND |
| | | 16.7 | 1.21 | −0.76 | |
| 1.25 | 30 | 25.46 | 24.61 | 24.62 | 24.52 gms |
| | 60 | 26.91 | 25.53 | 25.16 | 24.63 |
| | 90 | 32.41 | 25.91 | 25.92 | — |
| | 120 | 36.06 | 26.01 | 26.23 | — |
| | 150 | 39.21 | — | 26.41 | — |
| | 180 | 42.45 | — | — | — |
| | | 16.99 | 1.4 | 1.79 | 0.11 |
| 1.5 | 30 | 25.31 | 24.31 | 24.69 | 24.56 |
| | 60 | 26.99 | 24.89 | 24.91 | 24.72 |
| | 90 | 33.21 | 25.21 | 25.13 | 24.81 |
| | 120 | 35.82 | 25.78 | 25.29 | — |
| | 150 | 38.91 | — | 25.51 | — |
| | 180 | 41.98 | — | — | — |
| | | 16.67 | 1.47 | 0.82 | 0.25 |
| 1.75 | 30 | 25.42 | 25.02 | 25.16 | ND |
| | 60 | 27.03 | 25.26 | 25.32 | ND |
| | 90 | 33.13 | 25.59 | 25.91 | ND |
| | 120 | 35.86 | 25.87 | 26.43 | ND |
| | 150 | 38.19 | 26.01 | 26.55 | ND |
| | 180 | 39.68 | — | 26.88 | ND |
| | | 14.26 | 0.99 | 1.72 | |
| 2.0 | 30 | 25.36 | 25.31 | 25.28 | 24.98 |
| | 60 | 26.02 | 000 | 000 | 25.16 |
| | 90 | 26.49 | 000 | 000 | 25.36 |
| | 120 | 26.73 | 000 | 000 | 25.67 |
| | 150 | 000 | 000 | 000 | — |
| | 180 | 000 | 000 | 000 | — |
| | | 1.37 | | | 0.69 |
| 2.5 | 30 | 25.42 | 25.46 | 25.78 | 25.61 |
| | 60 | 25.78 | 000 | 000 | 25.92 |
| | 90 | 25.96 | 000 | 000 | 26.21 |
| | 120 | 000 | 000 | 000 | 26.38 |
| | 150 | 000 | 000 | 000 | — |

TABLE 3-continued

| | | PLANT GROWTH RATES | | | |
|---|---|---|---|---|---|
| MILS | DAYS | CHEVRON 9650 | CHEVRON 9506 | DUPONT 550 | CHEVRON 5754 |
| | 180 | 000 | 000 | 000 | — |
| | | 0.54 | | | 0.77 |

ND - MEMBRANE MATERIAL NOT AVAILABLE (NO DATA)
— - PLANT MATERIAL DIED DUE TO DECICATION
000 - NO CHANGE FROM PREVIOUS RECORDING

TABLE IV

MOISTURE VAPOR TRANSMISSION RATES
CARBON DI-OXIDE TRANSMISSION RATES
OXYGEN TRANSMISSION RATES

| RESIN I.D. TARGET FILM GAUGE, MILS. | Hi-D 9560 | ACTUAL GAUGE | Hi-D 9506 | ACTUAL GAUGE | PE 5754 | ACTUAL GAUGE |
|---|---|---|---|---|---|---|
| SECTION I. MOISTURE VAPOR TRANSMISSION RATES GRAMS/100 IN. SQ./24 HRS. | | | | | | |
| 0.50 | 1.190 | 0.570 | 1.261 | 0.590 | 2.220 | 0.600 |
| 0.75 | 0.684 | 0.840 | 0.932 | 0.850 | 1.358 | 0.720 |
| 1.00 | 0.432 | 1.010 | 0.623 | 1.000 | 1.035 | 1.050 |
| 1.20 | 0.339 | 1.230 | 0.455 | 1.200 | 0.897 | 1.250 |
| 1.50 | 0.223 | 1.480 | 0.320 | 1.630 | 0.700 | 1.450 |
| SECTION II. CARBON DI-OXIDE TRANSMISSION RATES CC/100 IN. SQ./24 HRS. | | | | | | |
| 0.50 | 2093.5 | 0.525 | 2031.5 | 0.550 | 3097.5 | 0.500 |
| 0.75 | 1190.5 | 0.750 | 1396.5 | 0.800 | 2281.0 | 0.775 |
| 1.00 | 620.0 | 1.000 | 886.0 | 1.050 | 1587.5 | 1.050 |
| 1.20 | 450.5 | 1.225 | 622.0 | 1.225 | 1407.5 | 1.175 |
| 1.50 | 339.0 | 1.450 | 463.5 | 1.525 | 1246.5 | 1.500 |
| SECTION III. OXYGEN TRANSMISSION RATES CC/100 IN. SQ./24 HRS. | | | | | | |
| 0.50 | 1143.5 | 0.535 | 863.1 | 0.645 | 1556.5 | 0.625 |
| 0.75 | 424.4 | 0.795 | 746.0 | 0.745 | 1089.5 | 0.760 |
| 1.00 | 238.0 | 0.960 | 464.0 | 1.000 | 707.5 | 0.965 |
| 1.20 | 215.0 | 1.200 | 283.0 | 1.200 | 594.5 | 1.240 |
| 1.50 | 140.0 | 1.530 | 215.0 | 1.450 | 458.5 | 1.540 |

STAGE 1

Initial Tissue Culturing

The cultivars or parent plants to be micropropagated are maintained under carefully controlled greenhouse conditions in an attempt to yield plant tissue which minimizes the growth of microorganisms and particularly any biological contaminants. After selection of the optimal parent, an area of the plant with meristematic (undifferentiated) tissue is identified, and a bulk sample, which includes the meristematic tissue, is removed from the parent plant. This area is usually where active growth takes place, such as at the tips of stems or at lateral buds (between the leaf apex and the connection to the stem).

To prevent contamination of the culture by biological contaminants, the meristematic tissue is excised from the bulk sample and transferred to the growing medium under a laminar flow hood which removes airborne contaminants. Prior to the placement of the meristematic tissue sample into cellules 72 of integument pack 50, five ml of a suitable media (as distinguished from 10 ml in the prior art tissue culturing process) such as Murashige Minimal Organic Medium manufactured by Carolina Biological Supply Company is inserted into cellules 72. This medium is an agar-based substance containing all the required nutrients for tissue growth. Integument pack 50, containing the media therein, is then rolled and sterilized in an autoclave. This procedure tends to close the open upper side 78 of cellules 72. See FIG. 7. Later, under the laminar flow hood, the integument packs 50 are unrolled and its cellules 72 opened one at a time prior to tissue placement. A meristematic tissue sample, typically a 0.2 to 1.0 mm cube, is then placed into an individual cellule 72 of integument pack 50, a single cellule being shown in FIG. 4.

After tissue placement, the ports of entry into cellules 72 again tend to immediately close, reducing the length of time that the samples are exposed to the environment and that contaminants can enter. Thereafter, the upper ends 78 of cellules 72 are heat sealed at 80, thereby forming a complete investment and envelope around the plant tissue. In this state, the plant tissue is completely impermeable to contaminants as distinguished from the prior art containers.

The integument packs 50 are then exposed to approximately 300–500 foot-candles of light during this first stage.

Using the present inventive process, precise temperature and humidity conditions need not be maintained in the culture room. In the prior art process, as temperature changes occurred, atmosphere would be drawn into and expelled around the tops of the glass containers containing the tissue cultures, thereby increasing the risk of contaminations from airborne contaminants which had not been removed by the prior art air filtration system. Further, the 80% humidity level was typically maintained in the prior art in order to prevent the media from drying out through evaporation. Such is not critical in the inventive process. Furthermore, and importantly, the inventive process, as distinguished from the prior art process, can be carried out in an environment which does not require a sterile, filtered air-flow since each cellule 72 of the integument pack 50 is contaminant impermeable.

Once the tissue culture has been established, and it is growing in the initial culture and has been certified contaminant-free, it is ready for Stage 2.

STAGE 2

Tissue Culture Multiplication

During Stage 2, the initial tissue culture resulting from Stage 1 is multiplied. Under the laminar flow hood, the cellules 72 of the integument packs 50 of Stage 1 are opened with a sharp sterilized knife and the tissue samples, or portions thereof, are transferred to a second set of unused integument packs 50, an individual integument pack being shown in FIG. 7. Multiplication of the tissue culture occurs by using a different media. The media used for Stage 2 cultures differs from that used in Stage 1 culturing and includes hormones to induce rapid growth and multiplication of the tissue. Suitable Stage 2 media include Murashige Shoot Multiplication Mediums A, B, and C, available from the Carolina Biological Supply Company. Again, only 5 ml of media are required as compared to the 10 ml in the conventional prior art process. The integument packs 50 of Stage 2 are then heat sealed and suitably disposed on a rack within a culture room. About 300 to 500 foot-candles of light are provided. During this period, Stage 2 growth yields primarily non-differentiated tissue growth. The cells in each tissue sample multiply rapidly during Stage 2 to form a cluster of primarily undifferentiated tissue cells, the size of which depends upon the plant variety. The desired cell multiplication takes approximately 20 to 45 days, again depending upon the plant variety.

After each Stage 2 cycle, the integument packs containing the cultures are immersed in a solution of sodium hypochloride, rinsed, returned to the laminar flow hood, opened, and the tissue is removed. The tissue is then subdivided by cutting into a number of small pieces, each of which will then be cultured. Each time the tissue samples are divided, the individual smaller tissue samples are inserted into cellules 72 of unused integument packs 50. All of these steps are performed in the laboratory under a laminar flow hood.

Each culture is grown and divided in a 20 to 45 day cycle until a sufficient number of tissue samples have been produced to meet production goals. As an example, if each tissue culture emerging from Stage 1 produces a cluster of tissue which in turn yields five tissue samples capable of culturing, over 15,000 cultures will have been produced at the end of seven months of Stage 2 multiplication. With the exception of a few naturally occurring mutations or "sports," each of these resulting cultures of Stage 2 can then be grown into an individual plant which will be genetically identical to the parent plant. Thus, when the desired number of cultures have been produced in Stage 2, the tissue cultures then are ready for Stage 3 production.

STAGE 3

Differentiation and Plant Formation

During Stage 3, the cellules 72 of the integument packs 50 of Stage 2 are opened and tissue samples therein are divided and transferred to a third set of unused integument packs 50 as shown in FIG. 7. Although a single plant tissue growing into a plantlet is shown disposed within each individual cellule 72 in FIG. 7, during Stage 3, a plurality of plant tissues may be disposed within an individual cellule if desired. This may be done to save additional space. However, in the inventive process, the plantlets may be grown separately in the new integument packs 50, eliminating the need for plant separation and the damage associated with untangling roots and foliage of several individual plants.

During Stage 3, the individual tissue samples grown in Stage 2 are placed in a media which stimulates cell differentiation and the growth of individual plantlets, each plantlet developing roots and foliage. Suitable Stage 3 media includes Murashige Pre-Transplant Mediums, available from the Carolina Biological Supply Company. The purpose of Stage 3 is to grow individual plantlets and prepare them for greenhouse culture. As distinguished from the prior art process, during Stage 3, the same size or a larger size integument pack 50 can be used. Initially in Stage 3, the plants are still grown in the culture room during this phase of development, but they are placed under increased light conditions so as to promote photosynthesis and growth. Approximately 2000 foot-candles of light are provided. The differentiation and growth process of Stage 3 requires between 20 and 45 days depending upon the plant variety. Because the integument packs 50 are contaminant impermeable, once individual plantlets have formed, the plantlets can be removed to the greenhouse to harden during the later portions of Stage 3 and need not be housed in a culture room for the entire Stage 3 period. This can significantly reduce the time normally required for the hardening process and reduce the size of the culture room.

Some commercial growers will purchase their plants upon completion of Stage 3. Many, however, will wait until the plants have completed Stage 4, the final production stage. If purchased at the end of Stage 3, the plants produced by the inventive process need not be immediately planted. They may be maintained for up to one month simply by keeping the plantlets in their integument packs under conditions of reasonable temperature and light. This is advantageous in commercial production where the Stage 3 plants are sometime shipped directly to the grower, who may lack the time to plant them immediately. In the prior art, since the plantlets have been removed from the sterile environment of the culture room, the commercial grower must immediately remove the plantlets from the shipping containers, rinse them to remove the media in which the contaminants can thrive, and then plant the plantlets immediately. Because the plantlets purchased by growers at the end of Stage 3 are shipped and maintained in the integument packs 50, they are contaminant impermeable and, therefore, without the danger of contamination. The advantage in the new process is that the grower does not have to plant immediately. When the grower is ready to plant, he can simply slit the Stage 3 integument open, rinse and deposit the plantlet into the soil medium.

STAGE 4

Greenhouse Culture and Hardening

At Stage 4, the plantlets are removed from the integument packs 50 of Stage 3 and are transferred to a greenhouse where they are individually planted in a soil medium. The plant's tolerance to light must be increased so that the plant can adapt to its natural environment. This process is called "hardening" the plant. The plant's tolerance to light is gradually increased in Stages 3 and 4. During Stage 4, the plants are exposed to up to 8,000 foot-candles in the greenhouse where growth and hardening is to take place. The exposure of the foliage of the plant directly to the atmosphere permits the plantlet to later grow in its natural environment without the protection of the integuments used in Stages 1 to 3.

The soil used in Stage 4 is typically a pre-sterilized peat moss mix. Depending upon the type of plant, most commercial plants remain in the greenhouse 30 to 90 days before they are shipped to the grower.

Use of the inventive process permits all stages of the micropropagation process to be less time consuming than their prior art counterparts, because the new and improved integuments are more easily and quickly handled. Thus, more tissue culture samples can be processed per day. Further, because the integuments consume less space than prior art containers, the costs associated with the culture room and the greenhouse are reduced.

TABLES 1 AND 2

Table 1 compares the contamination rate using the inventive integuments and related process versus the prior art process and containers, in this instance test tubes, using different plants in an environment without sterile filtered air. The tissue samples were cultured for 28 days in each stage under identical conditions, except that 10 ml of media was used with the prior art containers, and 5 ml was used with each of the cellules 72 of the integument packs 50.

TABLE 1

| CONTAMINATIONS PER 200 CULTURES PER STAGE | | | | | |
|---|---|---|---|---|---|
| | STAGE 1 | | STAGE 2 | | STAGE 3 |
| | Test Tube | Present Invention | Test Tube | Present Invention | Test Tube | Present Invention |
| Alocasia Lindanii (Alcoasia) | 66 | 25 | 55 | 0 | 51 | 0 |
| California (Boston Fern) | 61 | 29 | 59 | 0 | 52 | 0 |
| Hillii (Boston Fern) | 73 | 25 | 47 | 0 | 43 | 0 |
| Nephrolepis Biserrata Furcens (Fishtail Fern) | 68 | 28 | * | * | * | * |
| Boston Curly Frond (Boston Fern) | * | * | 52 | 12 | * | * |
| Boston Roosevelt Compacta (Boston Fern) | * | * | * | * | 44 | 0 |

*These Tables reflect the results of the limited tests which had been conducted at the time of this application. These tests were not conducted pursuant to a predetermined procedure whereby each plant underwent every stage of the microporpagation process. These tests were conducted using available tissue samples from a variety of plants, the tissue samples being in various stages of development. For this reason, certain stages of the micropropagation process were never conducted for certain plants.

TABLE 2

| TISSUE GROWTH RATES (AVERAGE WEIGHT PER SAMPLE) | | | | | |
|---|---|---|---|---|---|
| | STAGE 1 Note (1) | | STAGE 2 Note (2) | | STAGE 3 Note (1) |
| | Test Tube | Present Invention | Test Tube | Present Invention | Test Tube | Present Invention |
| Alocasia Lindanii (Alcoasia) | 0.38 g | 1.70 g | 1.03 g | 4.5 g | 1.52 g | 5.41 g |
| California (Boston Fern) | * | * | 1.03 g | 4.57 g | 1.31 g | 5.47 g |
| Hillii (Boston Fern) | * | * | 0.38 g | 4.38 g | 1.03 g | 5.05 g |
| Boston Curly Frond (Boston Fern) | * | * | 0.38 g | 4.08 g | * | * |
| Boston Roosevelt Compacta (Boston Fern) | * | * | * | * | 1.39 g | 4.68 g |

*These Tables reflect the results of the limited tests which had been conducted at the time of this application. These tests were not conducted pursuant to a predetermined procedure whereby each plant underwent every stage of the micorprogagation process. These tests were conducted using available tissue samples from a variety of plants, the tissue samples being in various stages of development. For this reason, certain stages of the micropropagation process were never conducted for certain plants.
Notes:
(1) Plants were grown for 28 days in Stages 1 and 3 using Murashige Minimal Organic in all cases.
(2) Plants were grown for 28 days in Stage 2 using Murashige Fern Multiplication in all cases except for the Alocasia Lindanii, where Murashige Shoot Multiplication A was used.

Tables 1 and 2 illustrate a reduction in contamination and an increase in growth rate and in the number of new tissue cultures and plantlets produced from an individual meristematic tissue of a cultivar using the inventive integuments and related process. For example, the Alocasia Lindanii of Table 1 shows that the prior art container and process had 172 contaminated tissue cultures per 600 cultures while the integument and process of the present invention had only 25 contaminated cultures. Thus, the present invention reduced contaminated cultures by approximately 85%. Table 2 shows that the growth of the Alocasia Lindanii culture using the integument and process of the present invention had an increase in average weight of approximately 4.5 times over the prior art process during Stage 1, an increase of approximately 4.4 times over the prior art process during Stage 2, and an increase of approximately 3.6 times over the prior art process during Stage 3. Over the three stages, the inventive integument and process produced a growth rate approximately 4 times greater than that of the prior art containers and process.

The following are further examples of the use of the new and improved integument and culturing process.

EXAMPLE I

Tissue Culture of *Nephrolepis Exaltata Whitmanii*

An experiment was conducted for the micropropagation of the fern *Nephrolepis Exaltata Whitmanii*, wherein the results of employing the integument and process of the present invention were compared with those obtained using the prior art containers and process. Stages 1 to 4 where utilizing the inventive integument and process are described first, followed by a description of the prior art containers and process.

Inventive Integument and Process

In preparing the media for Stage 1, 4.4 grams of premixed Murashige Minimal Organic medium and 30 grams sucrose were added to 500 ml of distilled water. The solution was stirred until the ingredients had dissolved. Additional distilled water was then added to bring the final volume of the solution to 1000 ml. The pH of the solution was then adjusted to 5.5. 8 grams of agar were then added and the mixture was heated until the agar dissolved. 5 ml of the media was then transferred to each of 200 cellules 72 of the integument packs 50. The unsealed ports of entry of the cellules were then covered with nonabsorbent paper towelling and the integument packs were autoclaved for fifteen minutes at 15 psi. The integuments were removed from the autoclave while still warm and placed under a laminar flow hood to complete cooling.

In preparing the meristematic tissue, 250 stolons of the fern were removed from the preselected parent plant and were wrapped in a sterile gauze. This gauze packet containing the stolons was then soaked with 500 ml of sterile distilled water to which two drops of wetting agent, such as Palmolive Green manufactured by Procter & Gamble of Cinncinati, Ohio, had been added.

This packet was sonicated for three minutes. The packet was then placed in a sterile container and covered with 500 ml of a 10% sodium hypochloride solution to which two drops of a wetting agent had been added. The container was covered with a tight fitting lid and vigorously shaken by hand for one minute. The container was then placed in the ultrasonic cleaner and sonicated for ten minutes, after which it was then removed and sprayed with a 90% isopropyl alcohol solution and placed in the laminar flow hood to air dry. The lid was removed and the 10% sodium hypochloride solution was drained off.

The gauze packet containing the stolons was then rinsed three times with sterile distilled water (approximately three minutes for each rinse). The packet was removed from the container, laid on a sterile work surface under the laminar flow hood, and the gauze packet was opened. The clean stolons were separated and approximately one inch of the active growing end was removed from each stolon. One active end was placed in each of the cellules 72 containing media.

The top of each cellule was heat sealed using a wire sealer at 300° F. for ten seconds. The integument pack was then labeled and the process was repeated until all the tissue had been so placed.

The integument packs were placed in the culture room, which was maintained at 80° F. with sixteen hours of light and eight hours of darkness per twenty-four hour period. The cultures were examined every twenty-four hours for contamination and growth.

During the first five days of Stage 1, twenty-six of the 200 cultures contaminated. At the end of ten days, some initial growth was observed in all of the remaining cultures. Some frond development was noted in all cultures by the end of the twentieth day, and the cultures were ready for Stage 2 multiplication by the end of the twenty-eighth day.

To prepare the media for Stage 2, 4.6 grams of premixed Murashige Fern Multiplication Medium and 30 grams of sucrose were added to 500 ml of distilled water. This was stirred until a solution was formed. Additional distilled water was added to bring the volume to 1000 ml. The pH was adjusted to 5.3. 8 grams of agar was then added to the solution and the solution was heated until the agar had dissolved. 5 ml of the solution was then added to each of 200 unused cellules 72 of integument packs 50. The open ports of entry of the cellules were covered with nonabsorbant paper towels and the integument packs were autoclaved for fifteen minutes at 15 psi. While still warm, the integument packs were moved to the laminar flow hood and allowed to cool.

To prepare the tissue cultures from Stage 1, the integument packs containing active clean cultures from Stage 1 were first completely immersed in a 10% sodium hypochloride solution for three minutes, then removed and rinsed with sterile water. The integument packs were dried with a sterile paper towel and laid on a sterile work surface under the laminar flow hood.

One cellule was opened at a time, using a sterlized No. 11 scalpel, by making a lengthwise cut down the center of the cellule. The tissue samples were removed with sterilized instruments and placed on a sterile work surface. If more than one active growing point was present on the removed tissue sample, the sample was divided into individual growing points. These individual growing points were then planted in the prepared cellule containing the Stage 2 multiplication media. After the cellules were filled, they were sealed using the above-described wire heat sealer.

The Stage 2 integument packs were then labeled and moved to the culture room, which was maintained at 80° F. with sixteen hours of light and eight hours of darkness per twenty-four hours. The cultures were checked every 24 hours for contamination and growth.

During the 28 day test period no contamination was noted in any of the cultures. During the first ten days, accelerated growth was noted in all cultures. At the end of twenty-eight days, the cultures were ready for stage 3.

In preparing the media for Stage 3, 4.4 grams of premixed pretransplant medium was mixed with 30 grams of sucrose and added to 500 ml of distilled water. This was then stirred until the ingredients had dissolved. Additional distilled water was added to bring the volume to 1000 ml. The pH was then adjusted to 5.5. 8 grams of agar was added, and the solution was heated until the agar had dissolved. 5 ml of the media was placed in each unused Stage 3 cellule 72 of integument pack 50. The unsealed ports of entry of the Stage 3 cellules were then covered with non-absorbant paper towelling and the integument packs were autoclaved for fifteen minutes at 15 psi. While still warm, the integument packs were removed from the autoclave and placed in the laminar flow hood to finish cooling.

The tissue samples emerging from the Stage 2 cellules were used as the Stage 3 source materials. The Stage 2 integument packs were first immersed in 10% sodium hypochloride solution for three minutes, and then rinsed in distilled water. The integument packs were dried with sterile paper towelling and placed on a sterile work surface under the laminar flow hood. Each cellule of the integument pack was opened by cutting lengthwise down its center with a sterile scalpel. The tissue was removed, placed on a sterile work surface, and then rinsed with sterile water and blotted dry with sterile paper towelling. Each tissue sample was then weighed. The average weight per sample was 4.5 grams.

The tissue emerging from Stage 2 was then subdivided into as many pieces of active growing tissue as could feasibly support good Stage 3 growth. Each division was then placed in a cellule 72 of an unused integument pack 50 which was sealed using the wire sealer at 300° F. for ten seconds.

The integument packs were then labeled and moved to the culture room maintained at 80° F. with sixteen hours of light and eight hours of darkness per each twenty-four hours. The cultures were checked every twenty-four hours for contamination and growth.

During the twenty-eight day test of Stage 3, no contamination was observed in any culture. Root development was noted at the end of the first week and good frond development appeared by the end of the second week.

After twenty-eight days, the resulting plantlets were ready to enter Stage 4. Under the laminar flow hood, the plantlets were removed from the integument packs, rinsed with distilled water, blotted dry and weighed. The average weight was 5.4 grams per tissue sample.

The Prior Art Process

The media preparation for the prior art process was the same as described above, except that twice as much media was prepared, and, rather than being placed into the integuments of the present invention, 10 ml of media was placed into each of 200 25×150 mm sterilized test tubes. The tubes were capped with conventional plastic caps.

The tissue preparation for the *Nephrolepis Exaltata Whitmanii* was also the same as described above. However, the results obtained following Stage 1 were dramatically different. Twenty cultures became contaminated during the first 5 days, and an additional 26 were lost during the 28 day Stage 1 period. It was not until the 15th day that all tissue samples showed some growth, and by the 20th day only one half of the samples showed frond development.

The Stage 2 media was the same as that described above, except that, once again, twice as much was prepared and placed into each Stage 2 test tube. The Stage 1 test tubes could not be immersed in the sodium hypochloride solution because there would be leakage through the caps. Instead, under the laminar flow hood, their outer surfaces were sterilized by spraying with a 90% isopropyl alcohol solution before the tissue samples were removed from their Stage 1 test tubes and placed into Stage 2 containers.

During the first 5 days of Stage 2 growth, 18 cultures became contaminated, and an additional 38 samples were lost to contamination between the 14th and 28th days. It was not until the 10th day that accelerated growth in the samples was observed. The average weight per sample at the completion of the 28 day Stage 2 was only 1.03 grams as compared to 4.5 grams using the inventive integument and process.

For Stage 3, once again twice as much media as that used with the inventive process was prepared and placed into each Stage 3 test tube. Again, rather than immersing the Stage 2 test tubes in sodium hypochloride solution, the outer surface was sprayed with the alcohol solution while under the laminar flow hood.

During the first 5 days of Stage 3 growth, 18 cultures became contaminated, and an additional 35 samples were lost to contamination between the 14th and 28th days. Root development did not appear on the majority of samples until the 14th day, and minimal frond development did not appear until the 24th day. The average weight per sample at the completion of the 28 day Stage 3 was only 1.3 grams as compared to 5.4 grams using the inventive integument and process. At this point, the majority of the samples were not ready for transfer to Stage 4. It is estimated that such samples would have required approximately 45 days of Stage 3 growth to achieve the size and maturity necessary for transfer to Stage 4.

EXAMPLE II

Lettuce Production From Tissue Culturing

Lettuce was produced in tissue culture using the inventive integument and process, as described below.

The Stage 1 media preparation was the same as that described above for the *Nephrolepis Exaltata Whitmanii*.

A non-heading lettuce variety known as butter leaf was selected. This variety has a normal production time from seed of 45 to 50 days. Tissue was first removed from the apical dome of thirty greenhouse-raised plants. The leaves were stripped, and the roots were removed exposing the stem, which was rinsed in running water. The apical dome was then removed.

The apical dome was placed in a clean container and covered with 10% sodium hypochloride solution to which two drops of a wetting agent had been added. This was sonicated for ten minutes and the tissue was rinsed three times in sterile distilled water.

Under the laminar flow hood, final tissue samples, which were still covered with leaf, were excised from the primary apical dome of the plant and subdivided three to four times to yield 100 tissue samples. Each individual tissue sample was placed in the cellule 72 of an integument pack 50, already each containing 5 ml of Stage 1 media. Each cellule was then sealed using a wire sealer at 300° F. for ten seconds. The integument packs were labelled and moved to the culture room which was maintained at the same temperature and light conditions as described with respect to Example I. The cultures were examined every twenty-four hours for growth and contamination.

During the first five days, thirty-five cultures contaminated, but no further contamination occurred. On the fifth day, good root development was noted in all the remaining cultures, and by the end of the seventh day, all cultures had developed leaves and were actively growing. A tremendous increase in tissue mass was noted by the end of the tenth day, at which time a majority of the cultures had developed one inch long leaves. By the twenty-eighth day, the average leaf size was three inches, and all cultures were ready for Stage 2.

In preparing the media for Stage 2, 4.8 grams of Murashige Premixed Multiplication Medium A and 30 grams of sucrose were added to 500 ml of water. This was stirred until the ingredients had dissolved and distilled water was added to make the final volume 1000 ml. The pH was adjusted to 5.5. 8 grams of agar was then added to the solution, and it was heated until the agar had dissolved. 5 ml of media was put into each cellule 72 of integument packs 50. The open ports of entry of the cellules were covered with nonabsorbent paper towelling and the integument packs were autoclaved for fifteen minutes at 15 psi. While still warm, the integument packs were placed in the laminar flow hood to complete cooling.

The tissue samples emerging from Stage 1 were used for Stage 2 cultures.

The Stage 1 integument packs were completely immersed in a 10% sodium hypochloride solution for three minutes to effect surface sterilization. They were then rinsed in sterile water and dried with sterile paper towelling. Under the laminar flow hood, the cellules were individually opened by cutting lengthwise down the center, and the tissue was removed and placed in a sterile work surface under the laminar flow hood. All roots and leaves were removed from the tissue and, where possible, the remaining tissue was subdivided. The subdivided tissue samples were then placed into the unused Stage 2 integument packs, one tissue sample per cellule. After each cellule was filled, it was heat sealed with the wire sealer.

All integument packs were labelled and placed in the culture room, maintained at the light and temperature conditions as described with respect to Example I. The cultures were examined every twenty-four hours for growth and contamination.

No Stage 2 cultures were lost to contamination. By the end of the fifth day, there was a substantial increase in the tissue mass. By the tenth day, there was good root development along with primary leaf development. By the end of the fifteenth day, clearly defined plantlets were visible in locations which indicated that lateral buds had developed. The lateral buds continued to grow until the end of the twenty-eight day test period. By this time, well-developed plantlets were ready for additional subculture.

To prepare the media for Stage 3, 4.4 grams of pre-mixed transplant medium and 30 grams of sucrose were added to 500 ml of distilled water. The solution was stirred until the ingredients were dissolved. Additional distilled water was added to make the final volume 1000 ml. The pH was adjusted to 5.5.

50 ml of this media was dispensed into the alternative integument embodiment 90 specially designed to promote the growth of leafy vegetables. The integument employed was twelve inches long with a three inch long root chamber at the base.

The open ports of entry of the cellules 122 of integument 90 were folded over and closed with paper clips and the integuments 90 were then autoclaved for fifteen minutes at 15 psi. While still warm, the integuments were moved to the laminar flow hood to finish cooling.

The active tissue samples from Stage 2 were used as source materials. The Stage 2 integuments were immersed in a 10% sodium hypochloride solution for three minutes to effect surface sterilization, then rinsed in sterile water, dried with sterile paper towels, and laid on a sterile work surface under the laminar flow hood. The cellules 122 of the integuments 90 were opened by cutting lengthwise down their centers, after which the tissue was removed and placed on the sterile work surface.

Individual plantlets were then removed from the primary tissue mass, and were placed in the center of each of the integuments 90 specially designed for leafy vegetable growth. The top of each integument 90 was then sealed with the wire sealer at 300° F. for twenty seconds. The integuments were labeled and moved to the culture room which was maintained at the light and temperature conditions as described with respect to Example I.

No contamination was noted in any of the cultures. By the end of the fifth day, all cultures showed good root development. Leaf development was noted on the sixth day, and it progressed very rapidly. Leaves three inches long were observed in all cultures by the fifteenth day, and full leaf development was noted on the thirtieth day. Complete lettuce plants were harvested on the thirty-fifth day. All had well-developed leaves suitable for consumption. The plants averaged seven inches in length, this measurement being taken from the bottom of the lowest leaf to the top of the plant. The plants also had well-developed interiors with densely packed leaves. Normally, this type of lettuce is non-heading and it takes 45-50 days to produce a similar sized plant from seed.

EXAMPLE III

Lettuce Production from Seed

An experiment was conducted to determine whether the use of the integument and method of the present invention enhanced lettuce growth when lettuce was grown from seed. The experiment was conducted as described below.

The media used was Murashige Minimal Organic, with 30 grams of sucrose and 8 grams of agar dissolved therein by the techniques described above for *Nephrolepis Exaltata Whitmanii*. The final pH was adjusted to 5.5. 5 ml of the media was then placed into the cellules 72 of integument packs 50 depicted in FIG. 7.

Black-seeded Simpson lettuce was used. Two hundred commercially obtained seeds were wrapped in gauze and surface sterilized by sonicating for ten minutes in a 10% sodium hypochloride solution to which two drops of a wetting agent had been added. The gauze packet was then removed and rinsed three times in sterile distilled water, with each rinse lasting for three minutes. The gauze packet was then placed on a sterile work surface under a laminar flow hood and the seeds were separated into two equal groups of 100 each. One hundred of the seeds were planted in the cellules 72 of integument packs 50 with one seed per cellule 72.

After each cellule 72 was filled, it was sealed, labeled and placed in the culture room where it was checked daily for growth and contamination.

The other 100 seeds were planted in a seed starting mix consisting of peat moss, pearlite and vermiculite. The seed was sown on the top of the pre-moistened mix, and pressed into the soil. The flat was labeled and placed in the culture room under the same light and temperature conditions as the seeds planted in the integuments, the same conditions described in Example I.

In the first five days, three cultures in the integuments were lost to contamination. Root development was noted in all cellules by the end of the third day, and primary leaf development was noted on the fourth day. Well-developed seedlings were observed in the integuments on the fifth day.

By the end of the seventh day, no growth was noted in the planted seeds, and a problem was suspected. A microscopic observation revealed evidence of fungal attack on all the seeds. It is suspected that the surface sterilization of the seed removed some natural fungal defense mechanism. The experiment was terminated at this point and repeated as described below.

200 seeds of the black seeded Simpson were obtained as described above. This time, however, only the 100 seeds which were intended for planting in the integuments were treated with the sodium hypochloride solution and sonicated as described above. These 100 seeds were planted in cellules 72 of integument packs 50 containing the same media described above.

The other 100 untreated seeds were pressed into the freshly prepared pre-moistened soil mix described above. Both the integument packs 50 and the flats with the untreated seeds were then placed into the culture room, which was maintained an 80° F. with 16 hours of light and 8 hours of darkness per day. Both the integument packs and flats were checked daily for contamination and germination. The soil in the flats was misted daily to moisten the soil.

During the first five days, two cultures in the integument packs were lost to contamination. Root development was noted in the third day with primary leaf development occurring on the fourth day. Well-developed seedlings were observed on the fifth day. By the end of the tenth day, the seedlings in the integument packs had grown to over one inch in length and had well-developed root systems. At the end of the twenty day test period, these seedlings had filled the cellules of the integument packs with well-developed leaves. 98% of the seeds in the integument packs germinated.

Only 30% of the seeds planted in the soil mix first showed primary leaf development on the seventh day. By the end of the eighth day, only 68 of the 100 seeds had germinated. Root development was not observable as the roots were beneath the soil. The final resultant seedlings averaged only one inch in height with one to two secondary leaves. Eight additional seedlings were lost. At the end of the test, only 60% of the starting seeds originally planted in soil had produced seedlings.

While this experiment was conducted through the use of integument packs 50 such as illustrated in FIG. 7, given the high germination rates of the seeds grown using the inventive process, it is preferable to grow lettuce from seed in an integument 90 such that the plantlets produced would not have to be transferred from an integument pack 50 to an integument 90. Due to the low cost of the integument 90 and the seed itself, any integument 90 containing a seed which fails to germinate can easily be identified and disposed of. Further, eliminating the steps of transferring plantlets from integument packs 50 to integuments 90 would eliminate the significant labor costs otherwise incurred.

Example IV

Fungal and Bacterial Production and Culture Storage

Tests were conducted to determine if the integument and method of the present invention would allow for the growth, isolation and storage of bacterial and fungal cultures. The tests were performed in the manner described below:

Fungal Cultures

A semisolid Minimal Organic Media with 30 grams of sucrose and 8 grams agar was prepared by techniques described above for *Nephrolepis Exalata Whitmanii*. The final ph was adjusted to 5.5. 5 ml of the media was then placed into cellules 72 of integument packs 50 depicted in FIG. 7. The integument packs 50 were then autoclaved for 15 minutes at 250° F. at 15 p.s.i. They were then placed in the laminar flowhood and allowed to cool. Several cellules 72 of integument packs 50 were innoculated with *Rhizoctonia solani*. This was done by inserting a sterile inoculation loop into a pure culture of *Rhizoctonia solani*, removing it and then inserting it into a cellule 72 of integument pack 50. The innoculant loop was placed in the center of the cellule and moved down until contact was made with the media. The loop was then resterilized and the process repeated until all cellules 72 of integument pack 50 had been innoculated. The integument packs 50 were heat sealed, labeled and placed in the culture room. This process was repeated using pure cultures of *Rhizopus stolonifer* and *Penicillium italicum* on several integument packs 50.

To determine if cross contamination would occur between cellules 72 of integument pack 50, several integument packs were innoculated in the following manner. The first, third and fifth cellule 72 of the integument pack 50 was innoculated with *Rhizoctonia solani, Rhizopus stolonifer* and *Penicilliym italicum* respectively, leaving cellule 2 and 4 containing only sterile media. The integument packs were sealed and each cellule containing an innoculant was labeled. The integument packs were placed in the culture room.

After 5 days all cultures were checked by visual observation for growth of fungus. All innoculated cultures showed positive growth and no growth was observed on those cellules that were not innoculated. The cultures were checked several times during a six month period. While fungal growth slowed as the media was consumed, the cultures remained viable. Little or no drying of the media was noted. Further, the resulting fungal cultures appeared to be pure, i.e., uncontaminated from outside microorganisms or from the other fungal cultures.

Bacterial Culture

Several integument packs 50 were innoculated with the bacteria *Serratia marcescens*, obtained from a pure culture in the method described above for fungal cultures.

The cultures were checked by visual observation after 5 days and several times after that during a 6 month period. All innoculated cellules of the integuments showed positive growth of *Serratina marcescens*. It was observed for certain bacterial cultures that the bacteria migrated towards the inner surfaces of the integument membrane where the gas exchange with the ambient atmosphere was greatest. There was no bacterial growth or contamination of the cellules of the integuments that were not innoculated, and those that were innoculated appeared pure. At the end of a 6 month period all cultures were viable with little or no loss of media due to drying.

Certain microorganisms live and grow anaerobically Although no such experiments have yet been conducted, the integument for culturing these microorganisms can be made from less permeable materials than the polyethylene of the preferred embodiment so as to preclude a gaseous interchange between the ambient environment and the organic material. Similarly, some microorganisms prefer or require the absence of light. When culturing such microorganisms, an opaque material can be used for the membrane.

Examples I-III above demonstrate that the integument and method of the present invention yields dramatic improvements in plant micropropagation and tissue culturing. These same improvements will follow irrespective of whether the plants cultured are horticultural, agricultural or even aquatic in variety. It is believed that the invention will yield dramatic improvements in animal and human tissue culturing as well. Example IV demonstrates the ability of the integument and method described herein for culturing microorganisms, such as viruses, single celled algea, fungus and bacteria, and in preventing the cultured microorganisms from escaping from the integument and contaminating or infecting others.

The Examples and embodiments described are exemplary only and not limiting. Many variations and modifications of the processes and the integuments are possible, and are within the scope of the invention. Accordingly, the scope of protection is not limited by the above description but only by the claims which follow, and that scope includes all equivalents of the subject matter of the claims.

I claim:

1. A system for the culturing of organic material, said system comprising:
   plant tissue, seeds or plants;
   a medium for growing said plant tissue, seeds or plants;
   a container having walls made of Chevron HiD-9650 high density polyethylene for enclosing said plant tissue, seeds or plants and sealing said plant tissue, seeds or plants from biological contaminants; said container being gas permeable and liquid impermeable, thereby allowing gas exchange through said container for the culturing of said plant tissue, seeds or plants.

2. The system of claim 1 wherein the moisture vapor transmission rate of each said wall is less than 0.68 grams per 100 square inches per 24 hours at one atmosphere.

3. The system of claim 1 wherein said container will withstand autoclaving at a temperature of 250° F. at a pressure of 15 psi without deformation of said walls, whereby said container may be sterilized.

4. The system of claim 1 wherein each said wall is between one and two mils in thickness.

5. A system for the growing of organic material in an unsterile environment, said system comprising: a plant material, a growth medium, and a translucent, gas permeable and liquid impermeable membrane of high density polyethylene for enclosing said plant material and growth medium in a sterile atmosphere and sealing said plant material from the unsterile environment; said membrane having a molecular structure forming interstices smaller than a virus, a moisture vapor transmission rate of less than 0.68 grams per 100 square inches per 24 hours at one atmosphere and a resistance to withstand autoclaving at least at a temperature of 250° F. at a pressure of 15 psi without deformation.

6. The system of claim 5 wherein said membrane has a carbon dioxide transmission rate between 200 and 1190 cubic centimeters per 100 square inches per 24 hours at one atmosphere.

7. The system of claim 5 wherein said membrane has an oxygen transmission rate between 100 and 424 cubic centimeters per 100 square inches per 24 hours at one atmosphere.

8. The system of claim 5 wherein said membrane is a single layer of high density polyethylene film.

9. The system of claim 5 wherein said membrane has interstices no greater than 0.01 micrometers in size.

10. A culturing system for micropropagation, said system, comprising:
    a plant tissue;
    a growth medium;
    a Chevron HiD-9650 high density polyethylene material forming at least one chamber, said chamber being made entirely of said material;
    said material having a predetermined transmission rate for oxygen, carbon dioxide, and moisture vapor and interstices no greater than 0.01 micrometers in size for preventing viral passage therethrough; and
    said chamber having an aperture for receiving said plant tissue and media, said aperture being adapted for closure after said chamber receives said plant tissue and media.

11. The culturing system of claim 10 wherein said chamber is formed by attaching at predetermined locations adjacent layers of said polyethylene material.

12. The culturing system of claim 11 wherein said chamber is formed by one sheet of said polyethylene folded over and heat sealed along its open sides.

13. The culturing system of claim 11 wherein said adjacent layers of polyethylene are heat sealed to form a plurality of chambers.

14. An integument pack for micropropagation, said integument pack comprising:
    plant tissue;
    growth medium;
    adjacent layers of semipermeable and translucent high density polyethylene material being attached together at predetermined locations thereof to form a plurality of cellules for receiving said plant tissue and growth medium;
    said cellules being adapted for closing upon receiving said plant tissue and growth medium whereby the tissue is completely enclosed from the ambient environment; and
    said semipermeable and translucent material having a molecular structure forming interstices sized to allow the diffusion of oxygen and carbon dioxide therethrough but preventing the passage of viral biological contaminants;
    said material having a moisture vapor transmission rate of less than 0.68 grams per 100 square inches per 24 hours at one atmosphere, an oxygen transmission rate between 100 and 424 cubic centimeters per 100 square inches per 24 hours at one atmosphere, and a carbon dioxide transmission rate between 200 and 1190 cubic centimeters per 100 square inches per 24 hours at one atmosphere.

15. A method for culturing plant material in an integument, said method comprising the steps of:
    inserting the plant material and a growth medium in a cellule of the integument, said cellule being made entirely of a semipermeable and translucent high density polyethylene membrane and having a molecular structure forming interstices smaller than a virus;
    enclosing the plant material within the cellule;
    sealing the plant material from the biological contaminants in the ambient environment;
    transmitting oxygen through the membrane at a rate between 100 and 424 cubic centimeters per 100 square inches per 24 hours at one atmosphere;
    transmitting carbon dioxide through the membrance at a rate between 200 and 1190 cubic centimeters per 100 square inches per 24 hours at one atmosphere; and
    transmitting moisture vapor through the membrane at a rate no greater than 0.68 grams per 100 square inches per 24 hours at one atmosphere.

16. A method of micropropagation, said method comprising the steps of:
    placing within a cellule having sides made of a gas-permeable, translucent high density polyethylene and a molecular structure forming interstices smaller than a virus, a growth medium which is suitable for establishing an initial culture;

placing a plant tissue sample within the cellule and sealing the plant tissue sample and growth medium from biological contaminants in the ambient environment;

transmitting oxygen through said sides at a rate between 100 and 424 cubic centimeters per 100 square inches per 24 hours at one atmosphere;

transmitting carbon dioxide through said sides at a rate between 200 and 1190 cubic centimeters per 100 square inches per 24 hours at one atmosphere; and transmitting moisture vapor through said sides at a rate no greater than 0.68 grams per 100 square inches per 24 hours at one atmosphere;

establishing an initial culture;

transferring a portion of the plant tissue sample to a second cellule having sides made of high density polyethylene and having a multiplication medium therein;

transmitting oxygen through said sides at a rate between 100 and 424 cubic centimeters per 100 square inches per 24 hours at one atmosphere;

transmitting carbon dioxide through said sides at a rate between 200 and 1190 cubic centimeters per 100 square inches per 24 hours at one atmosphere; and transmitting moisture vapor through said sides at a rate no greater than 0.68 grams per 100 square inches per 24 hours at one atmosphere;

multiplying the transferred portion of the plant tissue sample into a plurality of resulting plant tissue samples; and transferring one of the plurality of resulting plant tissue samples to a third cellule made of high density polyethylene having therein a medium suitable for individual plant formation.

17. A method of formation of a leafy vegetable from a seed, said method comprising:
   (a) inserting a solution of a growth medium into a cellule having sides made of a gas-permeable, translucent high density polyethylene and a molecular structure forming interstices smaller than a virus;
   (b) inserting a seed into the cellule;
   (c) enclosing the seed within the cellule and sealing the seed from biological contaminants in the ambient environment;
   (d) transmitting oxygen through said sides at a rate between 100 and 424 cubic centimeters per 100 square inches per 24 hours at one atmosphere;
   (e) transmitting carbon dioxide through said sides at a rate between 200 and 1190 cubic centimeters per 100 square inches per 24 hours at one atmosphere; and
   (f) transmitting moisture vapor through said sides at a rate no greater than 0.68 grams per 100 square inches per 24 hours at one atmosphere;
   (g removing the resultant plantlet from the cellule upon development of foliage and a root system.

18. The method of claim 17, further comprising:
   (e) transferring the plantlet to a foliage chamber in a leafy vegetable cellule, with the root system of the plantlet extending into a root chamber, said root chamber containing the growth medium; and
   (f) removing the leafy vegetable from the leafy vegetable cellule.

* * * * *